(12) United States Patent
Goldman

(10) Patent No.: US 12,097,120 B2
(45) Date of Patent: Sep. 24, 2024

(54) BONE IMPLANT DEVICE

(71) Applicant: Sleep Mechanics LLC, Boulder, CO (US)

(72) Inventor: Andrew Goldman, Boulder, CO (US)

(73) Assignee: Sleep Mechanics LLC, Boulder, CO (US)

(*) Notice: Subject to any disclaimer, the term of this patent is extended or adjusted under 35 U.S.C. 154(b) by 71 days.

(21) Appl. No.: 17/688,346

(22) Filed: Mar. 7, 2022

(65) Prior Publication Data
US 2023/0277324 A1 Sep. 7, 2023

(51) Int. Cl.
*A61F 2/30* (2006.01)
*A61F 2/48* (2006.01)

(52) U.S. Cl.
CPC ............ *A61F 2/3099* (2013.01); *A61F 2/482* (2021.08); *A61F 2002/30079* (2013.01); *A61F 2002/30224* (2013.01); *A61F 2002/30548* (2013.01); *A61F 2002/30565* (2013.01); *A61F 2002/30584* (2013.01); *A61F 2002/30624* (2013.01); *A61F 2002/30991* (2013.01); *A61F 2002/30993* (2013.01)

(58) Field of Classification Search
CPC .......... A61F 2/3099; A61F 2002/30991; A61F 2002/30993
See application file for complete search history.

(56) References Cited

U.S. PATENT DOCUMENTS 6,263,877 B1   6/2001   Gall
6,766,802 B1   1/2004   Keropian
7,451,767 B2   11/2008  Keropian
(Continued)

FOREIGN PATENT DOCUMENTS

BE    1028300 B1 * 12/2021
CA    2853072 C    5/2018
(Continued)

OTHER PUBLICATIONS

Sleepfoundation, "Best Anti-Snoring Mouthpieces and Mouthguards of 2022", Retrieved from https://www.sleepfoundation.org/best-anti-snoring-mouthpieces-and-mouthguards, Jun. 16, 2022, pp. 9.
(Continued)

*Primary Examiner* — Ariana Zimbouski
*Assistant Examiner* — Yasniary De La Caridad Morales
(74) *Attorney, Agent, or Firm* — DLA PIPER LLP (US)

(57) ABSTRACT

Systems, methods, and apparatuses for relieving upper airway obstructive breathing in a patient are disclosed. In some implementations, the apparatus comprises first and second pivot devices anchored to a mastoid bone and a mandible bone, respectively; an implant positioned between the first and second pivot device, the implant comprising a first end coupled to the first pivot device and a second end coupled to the second pivot device; an inactive position, the inactive position enabling a posterior displacement of the second end relative to the first end; an active position, the active position preventing posterior displacement of the second end relative to the first end, and anteriorly positioning the second end relative to the first end; and an activation mechanism enabling transition between the inactive position and the active position, and vice versa.

28 Claims, 10 Drawing Sheets

(56) References Cited

U.S. PATENT DOCUMENTS

| | | |
|---|---|---|
| 7,861,722 B2 | 1/2011 | Keropian |
| 7,954,494 B1 | 6/2011 | Connor |
| 8,062,032 B2 | 11/2011 | Bulloch et al. |
| 8,132,567 B2 | 3/2012 | Keropian |
| 8,146,600 B2 | 4/2012 | Pflueger et al. |
| 8,256,426 B2 | 9/2012 | Abramson |
| 8,302,609 B2 | 11/2012 | Martinez |
| 8,307,831 B2 | 11/2012 | Rousseau |
| 8,387,620 B1 | 3/2013 | Vaska et al. |
| 8,474,462 B2 | 7/2013 | Makower et al. |
| 8,561,616 B2 | 10/2013 | Rousseau et al. |
| 8,622,061 B2 | 1/2014 | Zhang et al. |
| 8,656,921 B2 | 2/2014 | Zhang et al. |
| 8,667,970 B2 | 3/2014 | Podmore et al. |
| 8,739,794 B2 | 6/2014 | Cutler |
| 8,783,258 B2 | 7/2014 | Jacobs et al. |
| 8,783,263 B2 | 7/2014 | Baldwin |
| 8,833,374 B2 | 9/2014 | Fallon et al. |
| 8,881,733 B1 | 11/2014 | Harkins |
| 9,017,070 B2 | 4/2015 | Parker |
| 9,161,855 B2 | 10/2015 | Rousseau et al. |
| 9,211,210 B2 | 12/2015 | Roue et al. |
| 9,242,118 B2 | 1/2016 | Brawn |
| 9,254,219 B2 * | 2/2016 | Shantha ................ A61F 5/566 |
| 9,314,320 B2 | 4/2016 | Urbanek |
| 9,517,087 B2 | 12/2016 | Montejo |
| 9,801,755 B2 | 10/2017 | Summer |
| 9,833,353 B2 | 12/2017 | Witt et al. |
| 10,064,706 B2 | 9/2018 | Dickerson |
| 10,195,010 B2 | 2/2019 | Sanders |
| 10,258,433 B2 | 4/2019 | Ergun |
| 10,285,784 B2 | 5/2019 | Robichaud |
| 10,299,892 B2 | 5/2019 | Alyami |
| 10,363,160 B2 | 7/2019 | Baratier et al. |
| 10,441,457 B2 | 10/2019 | Friedman et al. |
| 10,517,701 B2 | 12/2019 | Boronkay |
| 10,537,463 B2 | 1/2020 | Kopelman |
| 10,543,119 B2 | 1/2020 | Ingemarsson-Matzen |
| 10,575,981 B2 | 3/2020 | Rayek et al. |
| 10,582,995 B2 | 3/2020 | Gildener-Leapman et al. |
| 10,588,776 B2 | 3/2020 | Cam et al. |
| 10,595,971 B2 | 3/2020 | Parker |
| 10,631,959 B2 | 4/2020 | Shatkin |
| 10,772,756 B2 | 9/2020 | Vaska et al. |
| 10,772,757 B1 | 9/2020 | Harris |
| 10,898,369 B2 | 1/2021 | Farrell |
| 10,945,814 B2 | 3/2021 | Carriere Lluch |
| 10,945,875 B2 | 3/2021 | Stenberg et al. |
| 10,980,585 B2 | 4/2021 | Marcus |
| 11,000,324 B1 | 5/2021 | Marcus |
| 11,007,076 B1 | 5/2021 | Hamrah et al. |
| 11,033,421 B1 | 6/2021 | Davis |
| 11,166,841 B1 | 11/2021 | Martinez |
| 2010/0239995 A1 | 9/2010 | Williams |
| 2011/0144558 A1 * | 6/2011 | Rousseau .............. A61F 5/0013 604/8 |
| 2012/0103345 A1 | 5/2012 | Gay |
| 2012/0145166 A1 | 6/2012 | Fallon et al. |
| 2015/0216716 A1 | 8/2015 | Anitua Aldecoa |
| 2017/0020715 A1 | 1/2017 | Walker et al. |
| 2017/0189223 A1 | 7/2017 | Summer |
| 2018/0368944 A1 | 12/2018 | Sato et al. |
| 2019/0000592 A1 | 1/2019 | Cam et al. |
| 2019/0000593 A1 | 1/2019 | Cam et al. |
| 2019/0274871 A1 | 9/2019 | Veis et al. |
| 2019/0374315 A1 | 12/2019 | Itsuki |
| 2020/0146782 A1 | 5/2020 | Cope |
| 2020/0155339 A1 | 5/2020 | Cam et al. |
| 2020/0222158 A1 | 7/2020 | Coreil et al. |
| 2020/0289239 A1 | 9/2020 | Raby et al. |
| 2020/0315839 A1 * | 10/2020 | Sanders ................... A61F 2/00 |
| 2020/0383710 A1 | 12/2020 | Kaveh et al. |
| 2020/0405449 A1 | 12/2020 | Kaveh |
| 2021/0007831 A1 | 1/2021 | Hamm |
| 2021/0275346 A1 * | 9/2021 | Ow ....................... A61M 16/20 |
| 2022/0409376 A1 * | 12/2022 | Dimitroulis ........... A61F 2/3099 |

FOREIGN PATENT DOCUMENTS

| | | | |
|---|---|---|---|
| CN | 109789000 A | 5/2019 | |
| EP | 3103420 B1 | 11/2017 | |
| EP | 3644891 A1 | 5/2020 | |
| FR | 3011460 A1 | 4/2015 | |
| WO | WO-2007106358 A2 * | 9/2007 | ......... A61B 17/8071 |
| WO | 2010036875 A1 | 4/2010 | |
| WO | 2010087824 A1 | 8/2010 | |
| WO | 2019140531 A1 | 7/2019 | |
| WO | 2021091596 A1 | 5/2021 | |

OTHER PUBLICATIONS

Vitalsleep, "Vitalsleep_Anti-Snoring_Mouthpiece", Retrieved from https://www.vitalsleep.com/products/vitalsleep-snoring-mouthpiece?utm_source=googleshopping&utm_medium=cse&kw=&cpn=12628532617&gc_id=12, Jun. 16, 2022, pp. 3.

* cited by examiner

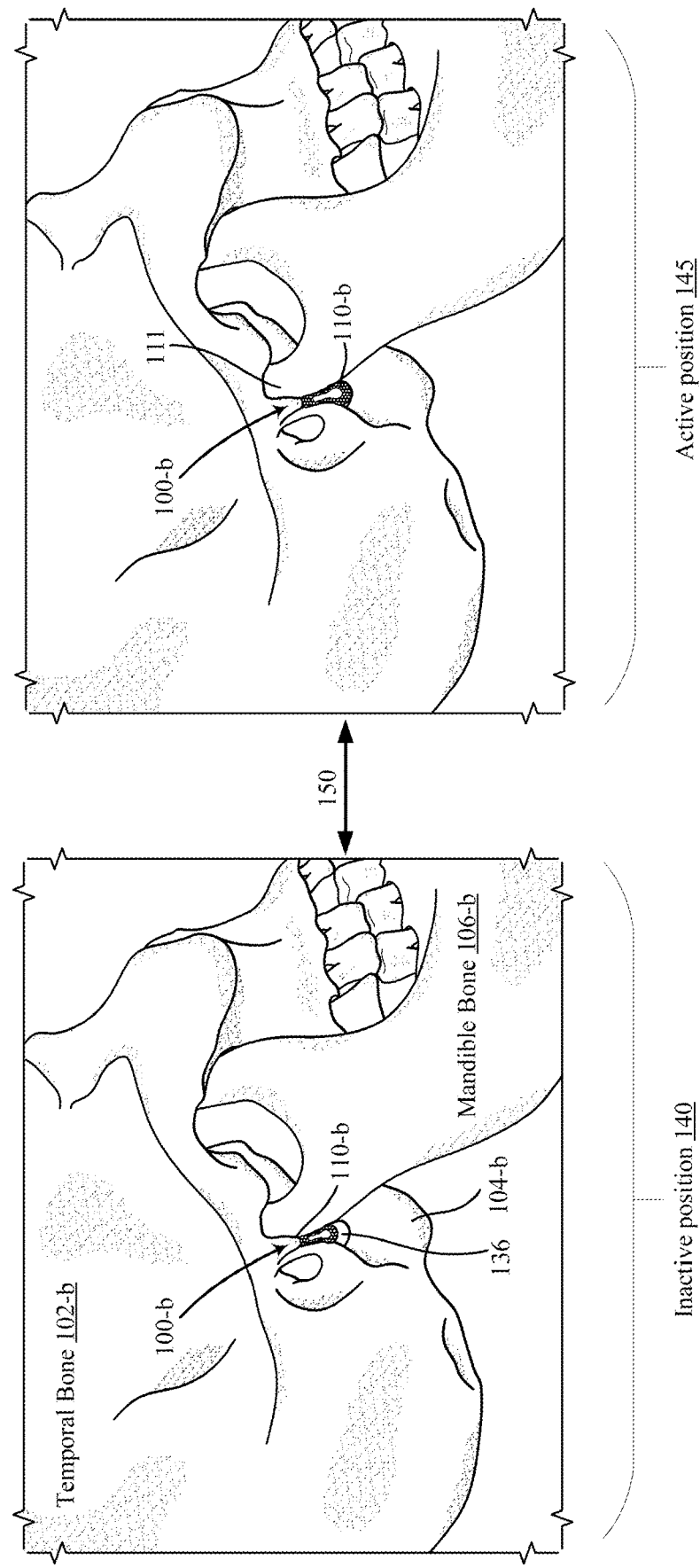

BONE IMPLANT DEVICE

FIELD OF THE DISCLOSURE

The present disclosure relates generally to implant devices. In particular, but not by way of limitation, the present disclosure relates to devices, systems, and methods for relieving symptoms associated with upper airway obstructive breathing and snoring using bone implant devices.

BACKGROUND

Upper airway obstructive breathing may be characterized as complete or partial blockage of the upper airway during sleep. Common medical conditions associated with upper airway obstructive breathing may include sleep disordered breathing, sleep apnea, and snoring, to name a few. The obstruction may be caused by relaxation of soft tissues and muscles in or around the throat (e.g., soft tissues at the base of the tongue and throat, tonsils, uvula, and pharynx), most common during sleep when the body's muscles tend to relax. As a result, a patient's lower jaw (or mandible) is more susceptible to retrodisplacement, i.e., it settles in a relatively posterior position. In such cases, the risk of the soft tissues (e.g., at or near the base of the tongue, in the throat) collapsing and/or obstructing the upper airway is also increased. People suffering from upper airway obstructive breathing often report low quality sleep or sleep deprivation, which leads to excessive daytime sleepiness, chronic fatigue, headaches, and numerous non-sleep related medical issues.

SUMMARY

The following presents a summary relating to one or more aspects and/or embodiments disclosed herein. The following summary should not be considered an extensive overview relating to all contemplated aspects and/or embodiments, nor should the following summary be regarded to identify key or critical elements relating to all contemplated aspects and/or embodiments or to delineate the scope associated with any particular aspect and/or embodiment. Accordingly, the following summary has the sole purpose to present certain concepts relating to one or more aspects and/or embodiments relating to the mechanisms disclosed herein in a simplified form to precede the detailed description presented below.

Aspects of the present disclosure relate to an implant device that is anchored at one end of the device either on the mastoid bone or temporal bone (i.e., skull base) of the skull and at another end of the device to the mandible/lower jawbone, anywhere along the ramus (shown as ramus bone 756 in FIG. 7) or body (shown as body 759 in FIG. 7) of the mandible, with the intent of stabilizing the position or effecting a change in position (e.g., anteriorly or forward) of the mandible bone of the face. In some cases, the implant device may anchor at a location between the mastoid and temporal bones, e.g., in lieu of anchoring to the mastoid or the temporal bone. Other anchoring locations besides the mastoid or temporal bone are also contemplated in different embodiments, and the examples listed herein are not intended to be limiting. In some examples, the implant device (or simply, implant) helps push the lower jaw (i.e., mandible bone) anteriorly with respect to the upper jaw (i.e., maxilla bone), the mastoid bone, and/or the temporal bone. The implant may be activated, for instance, based on the position of the patient's head or jaw, via a magnetic activation mechanism, or via a mechanical or pressure-activated system. In some examples, activation may cause the implant to become more rigid, which may serve to push the lower jawbone forward and help maintain it in an anterior position, thus preventing the lower jawbone from shifting posteriorly during sleep. The implant may also help keep the patient's upper airway clear by supporting the patient's tongue, soft tissues at the base of the tongue, and/or soft tissues in the throat, in an anterior position or a neutral position, which results in less obstruction of the upper airway. In some cases, the implant device may utilize a tensioning mechanism, such as a spring, a mechanical biasing device with a non-linear load or a non-linear k-value, or any other applicable biasing device. In yet other cases, the implant device may inflate upon activation. In one non-limiting example of such a device, an air/fluid pump may provide compressed air (or another fluid or foam) into the implant to activate it. In such cases, deactivation of the implant device may comprise partial or complete deflation of the implant. It is further contemplated that the implant device may be surgically placed, for instance, by a head and neck surgeon, or an oral surgeon. In some examples, the implant device may be of sufficient length (i.e., sized) to bridge the gap between the mastoid or temporal bone and the mandible. Further, the implant device may be installed at different angles depending on the patient's anatomy.

Some embodiments of the disclosure may be characterized as an apparatus for relieving upper airway obstructive breathing in a patient, the apparatus comprising a first pivot device anchored to at least one of a mastoid bone and a temporal bone of the patient, a second pivot device anchored to a mandible bone of the patient, and an implant positioned between the first pivot device and the second pivot device. The implant further comprises a first end coupled to the first pivot device, a second end coupled to the second pivot device, an inactive position, wherein the inactive position enables a posterior displacement of the second end relative to the first end, and an active position, where the active position at least one of prevents posterior displacement of the second end relative to the first end and positions the second end of the implant anteriorly relative to the first end. The apparatus or implant further includes an activation mechanism, where the activation mechanism enables transition between the inactive position and the active position, and vice versa.

Some embodiments of the disclosure may be characterized as a system for relieving upper airway obstructive breathing in a patient, the system comprising a first pivot device anchored to at least one of a mastoid bone and a temporal bone of the patient, a second pivot device anchored to a mandible bone of the patient, and an implant positioned between the first pivot device and the second pivot device. In some examples of the system, the implant further comprises a first end coupled to the first pivot device, a second end coupled to the second pivot device, an inactive position, wherein the inactive position enables a posterior displacement of the second end relative to the first end, and an active position, wherein the active position at least one of prevents posterior displacement of the second end relative to the first end, and positions the second end of the implant anteriorly relative to the first end. In some examples, the system further comprise an activation mechanism, wherein the activation mechanism enables transition between the inactive position and the active position, and vice versa. In some examples of the system, the activation mechanism is coupled to or in communication with the implant and comprises at least one of a magnetic or an electromagnetic device, a spring, a piston assembly, a pump, and a reservoir. In some examples of the system, at least a portion of the activation mechanism is positioned in an interior of the patient.

Some embodiments of the disclosure may be characterized as a method for relieving upper airway obstructive breathing in a patient, the method comprising anchoring a first pivot device to at least one of a mastoid bone or a temporal bone of the patient, anchoring a second pivot device to a mandible bone of the patient, and positioning an implant between the first pivot device and the second pivot device. In some examples of the method, the implant comprises a first end coupled to the first pivot device, a second end coupled to the second pivot device, a longitudinal axis extending from the first end to the second end, an inactive position comprising the longitudinal axis in a generally horizontal position, wherein the inactive position enables a posterior displacement of the second end relative to the first end, and an active position comprising the longitudinal axis in a generally vertical position. In some examples of the method, the active position at least one of prevents posterior displacement of the second end relative to the first end and positions the second end of the implant anteriorly relative to the first end. In some examples of the method, the active position transitions the implant between the inactive position and the active position, and vice-versa.

These and other features, and characteristics of the present technology, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

BRIEF DESCRIPTION OF DRAWINGS

FIG. 1B illustrates the active and inactive positions of the first example of the surgical implant shown in FIG. 1A, according to various aspects of the disclosure.

DETAILED DESCRIPTION

Figure 1A:
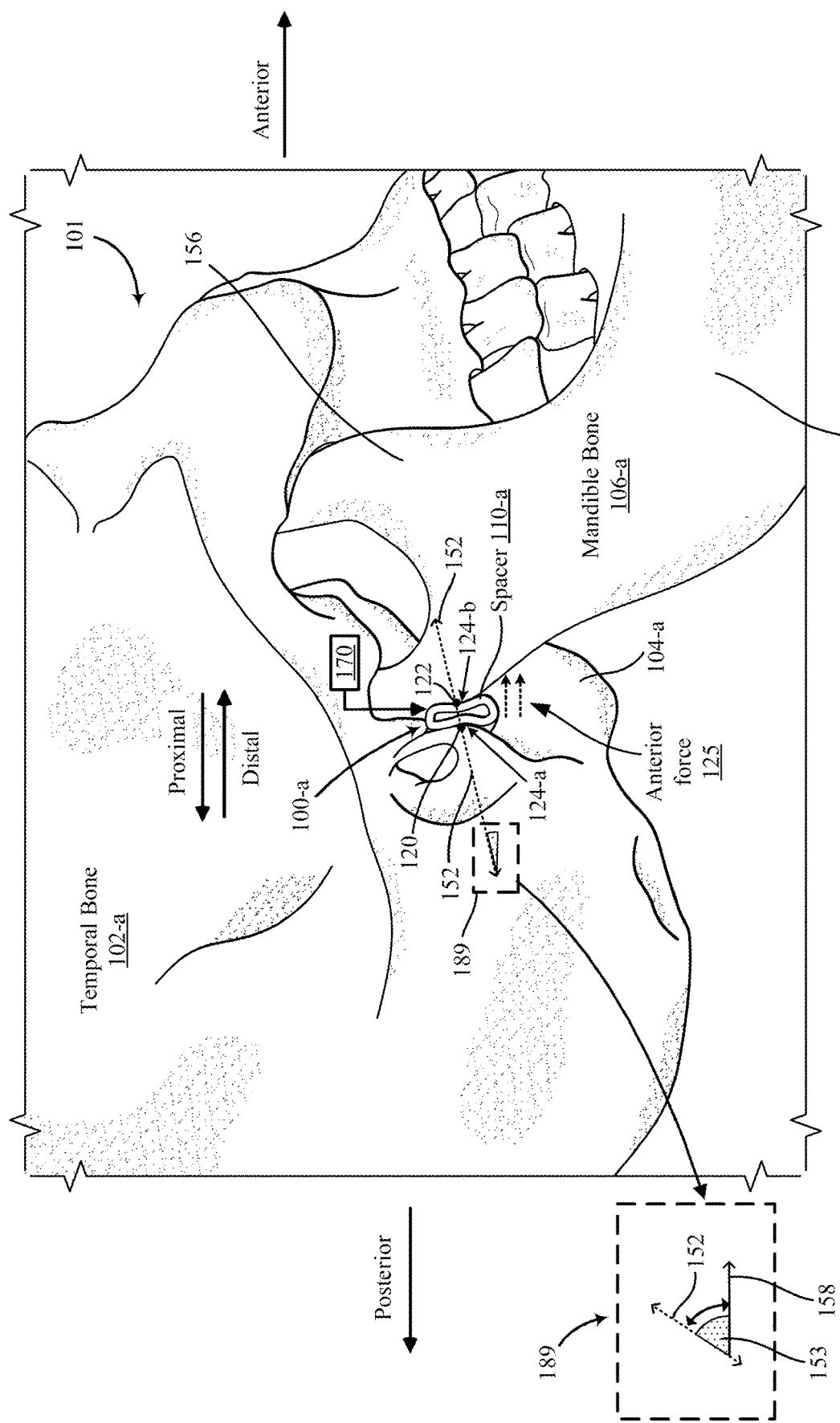
FIG. 1A illustrates a first example of a surgical implant device positioned in a patient's skull, according to various aspects of the disclosure.

The word "exemplary", and other similar terms, is used herein to mean "serving as an example, instance, or illustration." Any embodiment described herein as "exemplary" is not necessarily to be construed as preferred or advantageous over other embodiments.

The present disclosure relates generally to implant devices. More specifically, but without limitation, the present disclosure relates to systems, methods and apparatuses for relieving symptoms associated with upper airway obstructive breathing using an implant device. As used herein, the terms "surgical implant", "bone implant", "implant", "biasing member", and "implant device" may be used interchangeably throughout this disclosure. Further, the terms "anchor", "pivot device", and "anchoring device" may be used interchangeably throughout the disclosure.

Systems, methods, and apparatuses for relieving symptoms associated with upper airway obstructive breathing using a bone attachment-based implant device are described herein. The implant device may be used to treat upper airway obstructive breathing associated with sleep, such as, but not limited to, sleep disordered breathing, sleep apnea, and/or snoring. In some circumstances, when a user is in a horizontal or substantially horizontal position (e.g., laying down or sleeping, reclined backwards), their lower jaw (i.e., mandible) may be susceptible to retrodisplacement (e.g., backward shift, causing it to settle in a posterior position relative to when the user's spine is erect or substantially erect). This retrodisplacement is common during the deepest phases of sleep when the body's muscles are more relaxed. When this happens, the soft tissues at the base of the tongue and/or throat are more prone to collapse and obstruction, which can lead to sleep disordered breathing, snoring, sleep apnea, etc. In some examples, a bone-based implant device may be provided, where the implant device is anchored on the mastoid bone of the skull at a first end and on the mandible/lower jawbone at a second end. Alternatively, the bone-based implant device may be anchored at the first end on the temporal bone of the skull, or at a location between the mastoid and temporal bones. It should be noted that, the implant device may be placed unilaterally (i.e., anchored on one side of the user's skull), or alternatively, bilaterally (i.e., one implant anchored on each side of the user's skull).

The implant device may facilitate in relieving symptoms of upper airway obstructive breathing by maintaining the lower jawbone (or mandible) in a more neutral position, or by applying a force in the anterior/forward direction, which may help maintain airway patency by preventing the tongue, soft tissues in or around the throat, etc., from collapsing in the upper airway. Additionally, or alternatively, the implant may help prevent the mandible/lower jawbone from shifting posteriorly during sleep. In this way, the implant assists in maintaining airway patency by helping to keep the soft tissue at the base of the tongue and throat more open and unobstructed, which may serve to alleviate the symptoms and impact of upper airway obstruction.

Figure 2A:
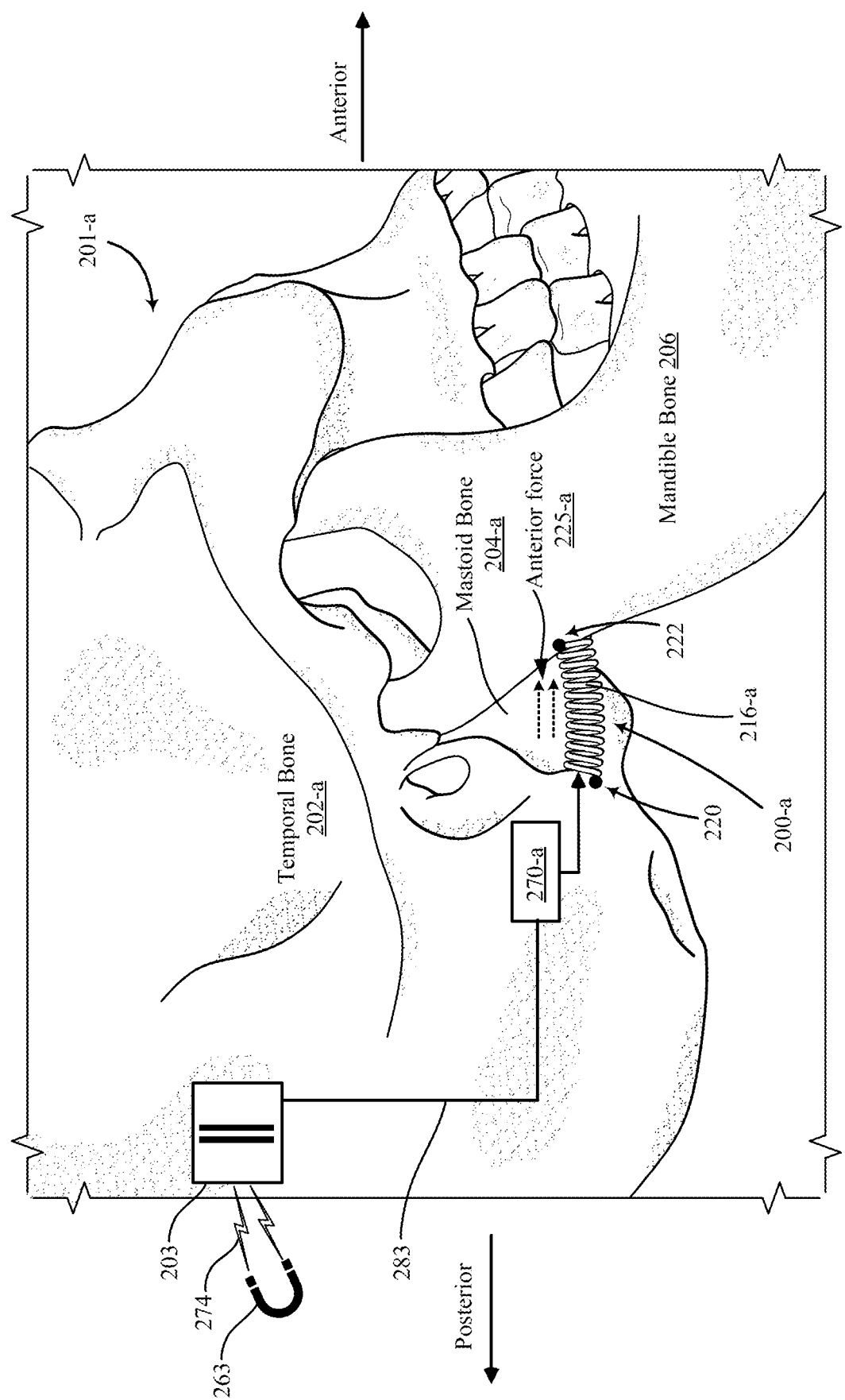
FIG. 2A illustrates a second example of a surgical implant device positioned in a patient's skull, according to various aspects of the disclosure.
Figure 4:
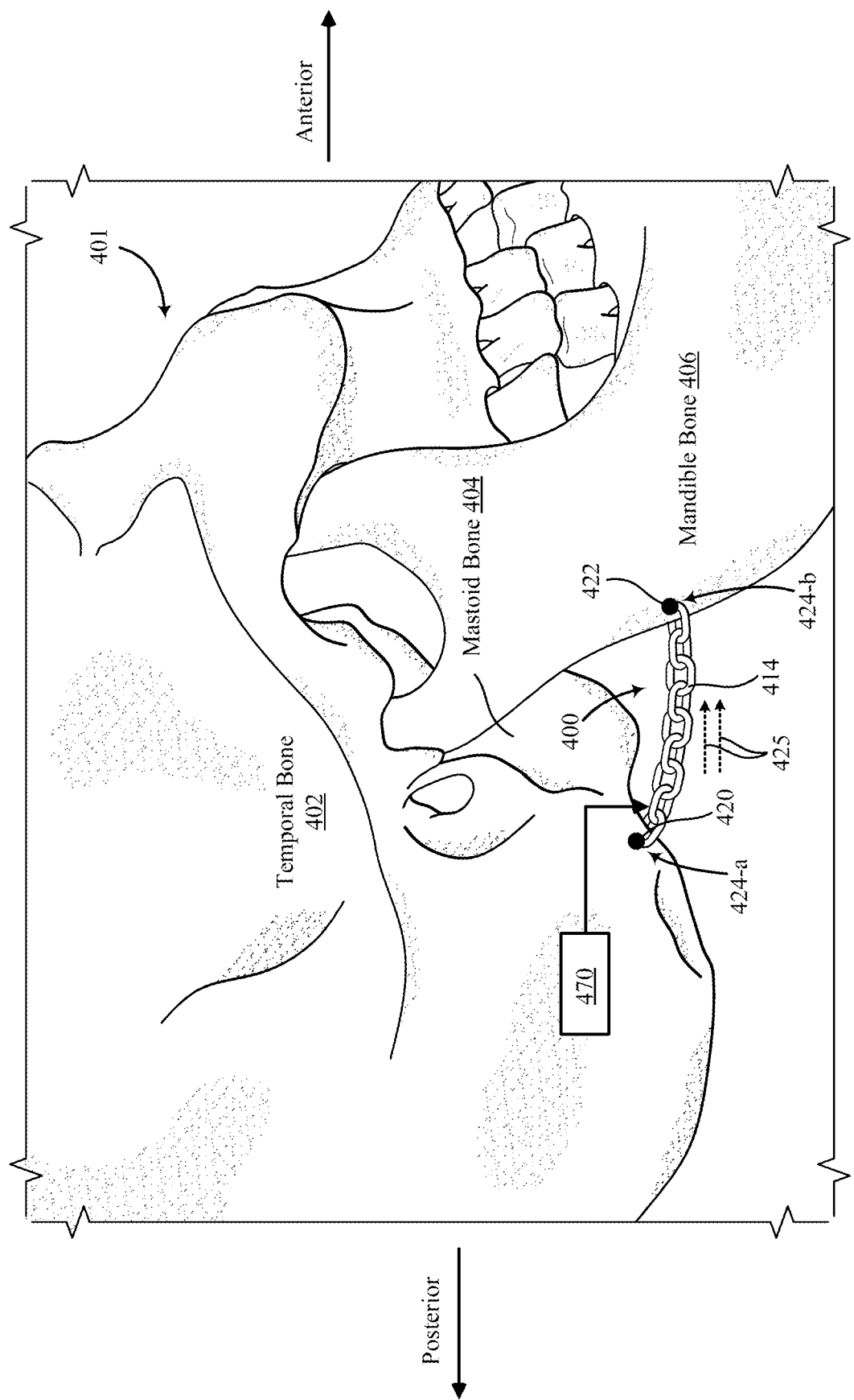
FIG. 4 illustrates a fourth example of a surgical implant device positioned in a patient's skull, according to various aspects of the disclosure.

In some cases, the implant device comprises an active position and an inactive position, where the transition between the active and inactive positions (and vice-versa) may be controlled via an activation mechanism (e.g., shown as activation mechanism 270-*a* in FIG. 2A, activation mechanism 470 in FIG. 4, etc.). In the active position, the implant device prevents posterior displacement of one end (e.g., an end anchored on the lower jawbone/mandible) of the implant relative to the other end (e.g., an end anchored on the mastoid bone or temporal bone). Additionally, or alternatively, in the active position, one end (e.g., an end anchored on the lower jawbone/mandible) of the implant may be positioned anteriorly relative to the other end (e.g., an end anchored on the mastoid bone or temporal bone).

Figure 3:
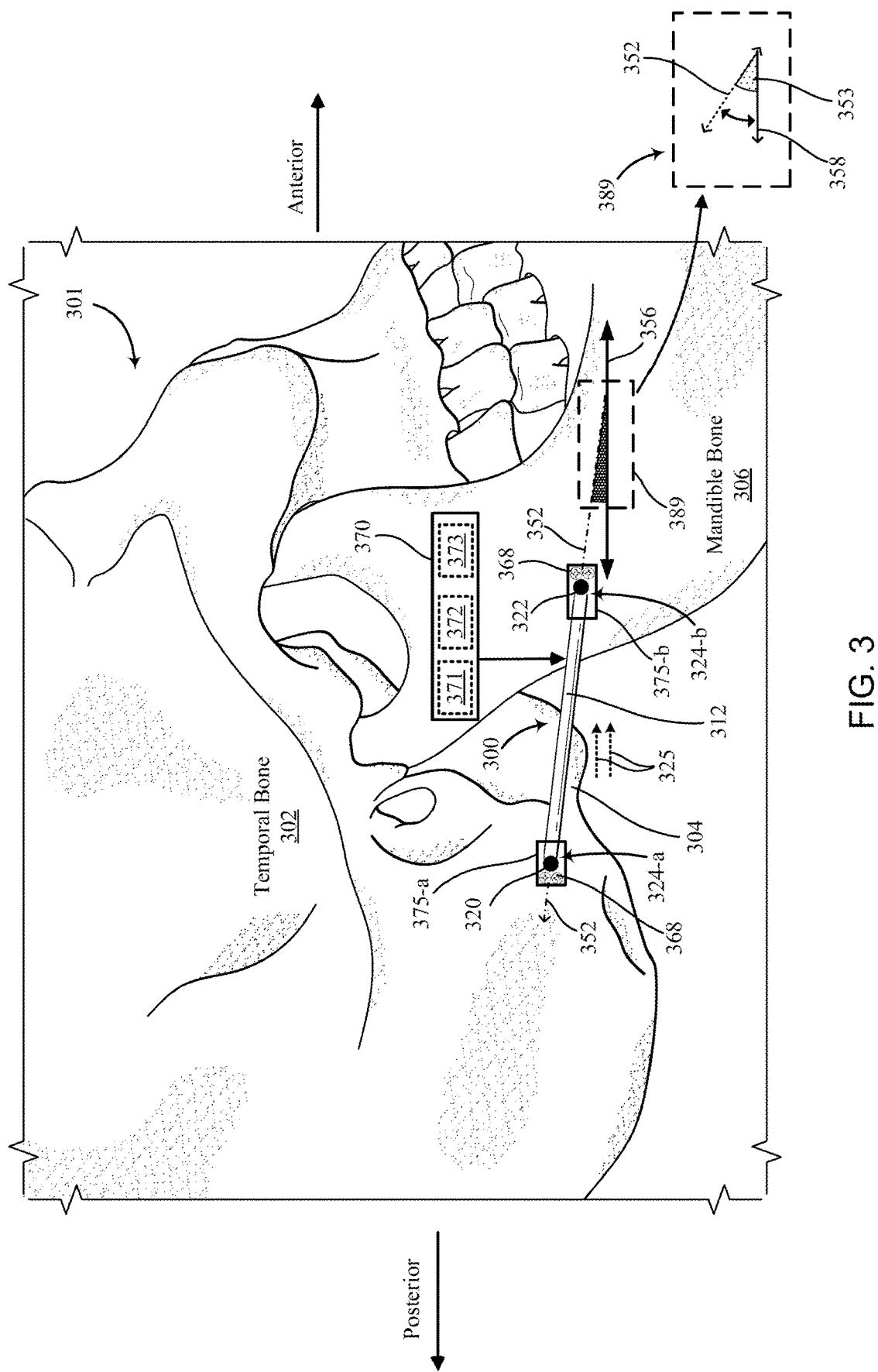
FIG. 3 illustrates a third example of a surgical implant device positioned in a patient's skull, according to various aspects of the disclosure.
Figure 8:
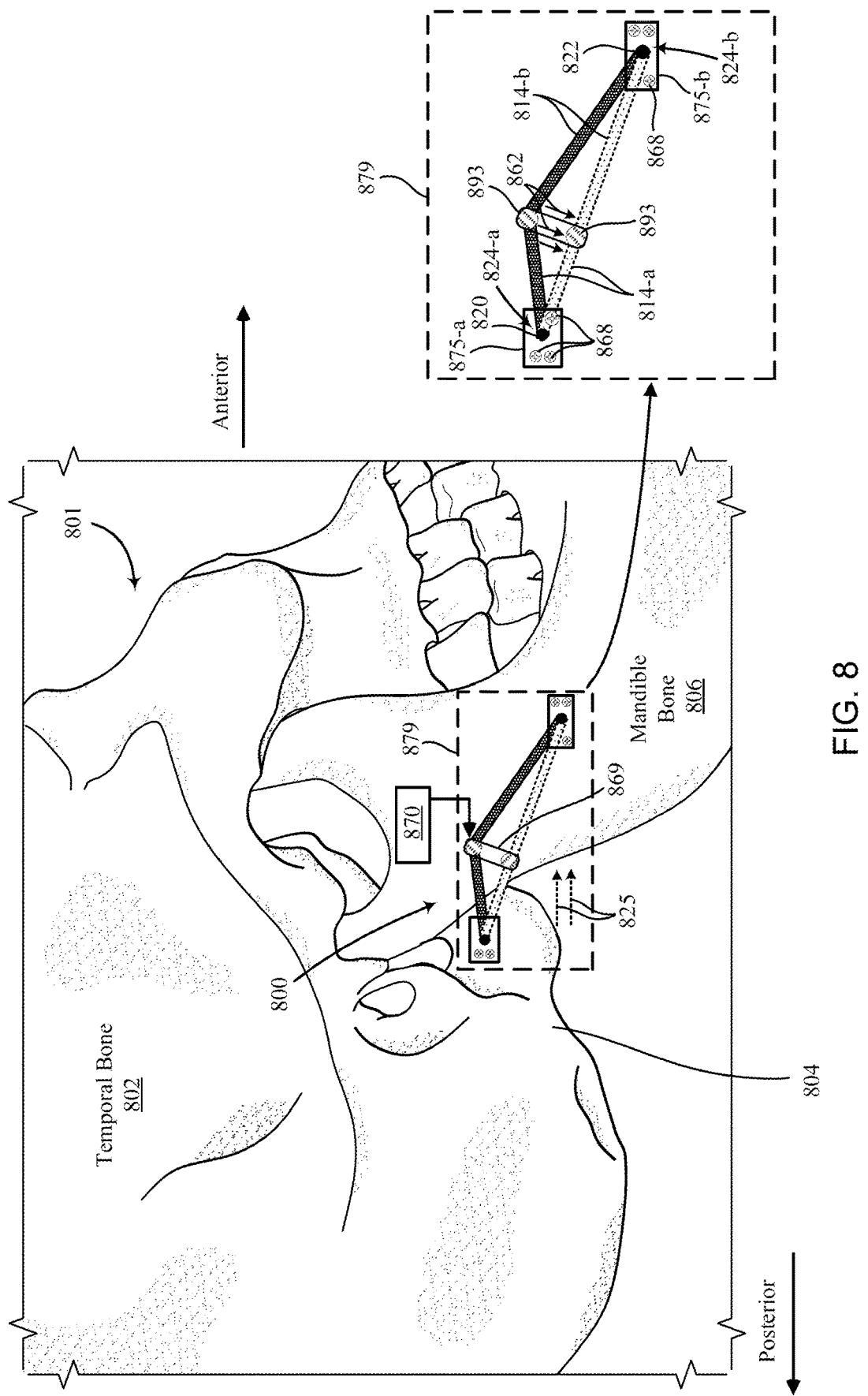
FIG. 8 illustrates a fifth example of a surgical implant device positioned in a patient's skull, according to various aspects of the disclosure.

In some cases, the implant device may be surgically anchored on the bones of the skull using a plating method (e.g., using one or more plates and screws, such as plates 375, 875 and screws 368, 868 in FIGS. 3 and 8), screws (or other types of fasteners), or any other applicable adhesive or clamping technique known in the art. It is further contemplated that at least a portion of activation mechanism may be surgically implanted with the patient (i.e., within an interior of the patient). The components (e.g., plates, screws, fasteners, etc.) used to couple the implant device and bones may be composed of surgical grade material. In one non-limiting example, the screws (e.g., screws 368, 868) and/or plates (e.g., plates 375, 875) may be composed of titanium or high-grade surgical stainless steel. Anchoring devices (e.g., shown as pivot devices 220, 222, 320, 322, in FIGS. 2A and 3, respectively) can include hardware suitable for fixation into bone, such as bone fasteners, screws, plates, rods, and connectors. The anchoring devices can be made of metal, composite, plastic, or any other suitable material, and/or combinations thereof. In some examples, an anchoring or pivot device can include a screw for securing the anchoring or pivot device to a patient's mastoid, temporal, and/or mandible bones. In some embodiments, one or more holes suitable for securing the pivot device, such as a surgical screw, can be drilled into the mastoid, temporal, and/or lower jawbones and used to secure the one or more pivot devices.

In some examples, the implant device provided herein may be coupled to one or more anchoring/pivot devices, where the anchoring/pivot devices are positioned in or on one or more anatomical structures of the patient's skull, such as the mastoid bone, temporal bone, a location between the mastoid and temporal bones, and/or lower jaw bones. By coupling the implant device to pivot devices attached to the bone, one or more force(s) (e.g., mandibular advancement forces) may be applied to the patient's mandible, which serves to reduce the likelihood of unwanted tooth repositioning (e.g., caused by long-term application of advancement and/or retraction forces on the teeth). In some embodiments, a pivot device can include a screw for securing the pivot device to a patient's mastoid bone, temporal bone, or lower jawbone. It should be noted that the pivot devices used to affix the implant to the mastoid bone and/or temporal bone, and the lower jaw bone may be the same or different. For instance, a first pivot device (i.e., anchoring device) anchored to the mastoid bone or temporal bone may comprise a bone fastener, while a second pivot device anchored to the mandible bone may comprise a rod. Alternatively, both the first pivot device and the second pivot device may comprise bone fasteners or screws. In some other cases, at least one of the first and the second pivot device may include a plate having a plurality of receiving holes for screws, where the plate is positioned on the corresponding bone. In yet other cases, the first pivot device may comprise a surgical screw and the second pivot device may comprise a plate having a sliding mechanism, and one or more screws for affixing the plate on the mandible bone. It is also contemplated that a pivot device may comprise a portion of the implant. It should be noted that the bone anchoring techniques described above are not intended to be limiting, and other means for bone anchoring are contemplated in different embodiments.

Various types of pivot devices (also referred to as anchoring devices) can be used in combination with the implants described herein to transition a rotational force (torque) and/or shear loads (e.g., due to normal wear and tear) to the bones (e.g., mandible bone). For example, the pivot device(s) may allow and/or constrain certain movements of the implant relative to the pivot device(s) when the implant is coupled to the pivot device(s). Constraint of translational and/or rotational movements can allow the implant to support bending and/or shear loads at or near the coupled pivot device(s). Optionally, a pivot device may permit certain movements while inhibiting other movements. For example, a rotatable pivot device (e.g., a pivot, ball joint, pin, etc.) can permit some or all rotational movements of a coupled implant relative to the pivot device while constraining some or all translational movements of the implant. In some embodiments, a rotatable pivot device (e.g., a pivot, ball joint) may permit rotational movement of the implant about to the pivot device with respect to three degrees of freedom in rotation (e.g., yaw, pitch, roll). Further, the rotatable pivot device may constrain some or all translational movement (e.g., along the longitudinal axis) of the implant relative to the pivot device. As another example, a partially rotatable pivot device can constrain some rotational movements (e.g., pitch or yaw) of a coupled implant. In some embodiments, a pivot device comprising a pin may allow rotation of the implant about the axis (i.e., longitudinal axis) of the pin only and constrain rotational movements in other directions. In some embodiments, a partially rotatable pivot device may constrain some or all translational movement of the implant relative to the pivot device. For instance, a pivot device comprising a pin may or may not permit translation of the implant along the longitudinal axis of the pin. In yet another example, non-rotatable pivot devices can constrain all rotational movements of a coupled implant. Additionally, or alternatively, non-rotatable pivot devices may constrain some or all translational movement(s) of the implant relative to the pivot device. In some examples, one of the pivot devices (e.g., a first pivot device anchored on the mastoid or temporal bone) may be rotatable, while the other of the pivot devices (e.g., a second pivot device on the mandible bone) may be non-rotatable.

FIG. 1A illustrates an apparatus 100-*a* for relieving upper airway obstructive breathing and/or for providing snoring relief, in accordance with aspects of the present disclosure. The apparatus 100-*a* is surgically implanted in or on bones of the patient's skull 101, according to various aspects of the disclosure. As seen, the patient's skull 101 includes a temporal bone 102-*a*, a mastoid bone 104-*a*, and a mandible bone 106-*a*. In the example shown, the apparatus 100-*a* comprises a first pivot device 120 coupled to at least one of a mastoid bone 104-*a* and a temporal bone 102-*a* of the patient. Further, the apparatus 100-*a* comprises a second pivot device 122 coupled to a mandible bone 106-*a* of the patient. The apparatus also includes an implant device (e.g., spacer 110-*a*) positioned between the first pivot device 120 and the second pivot device 122, where a first end 124-*a* of the spacer 110-*a* is coupled to the first pivot device and a second end 124-b of the spacer 110-a is coupled to the second pivot device. For example, the spacer 110-a may be positioned between a distal portion of the mastoid bone 104-a or the temporal bone 102-a and a proximal portion of the mandible bone 106-a. Further, the spacer may be shaped and sized to bridge a gap (e.g., shown as gap 136 in FIG. 1B) between the mastoid or the temporal bone and the mandible bone. As used herein, the terms "proximal" and "distal" may be used refer to the direction associated with the rear (or posterior) and front (or anterior) of the patient, respectively. For example, the term "proximal" may refer to the direction associated with the rear (i.e., backside) of the patient, while the term "distal" may refer to the direction associated with the front (i.e., face, chest) of the patient.

In some cases, the implant device or the spacer 110-a comprises an inactive position, where the inactive position enables a posterior displacement of the second end 124-b relative to the first end 124-a, and an active position, where the active position prevents posterior displacement of the second end relative to the first end and/or positions the second end of the spacer 110-a anteriorly relative to the first end. In accordance with various aspects of the present disclosure, the apparatus 100-a includes an activation mechanism 170 that enables transition between the inactive position and the active position, and vice versa. For instance, the activation mechanism 170 may activate the spacer 110-a based on a change in a position of the patient's skull (e.g., from a generally vertical position to a generally horizontal position). For example, as seen in FIG. 1B, there is a gap 136 between the mastoid bone 104-a or the temporal bone 102-b and the mandible bone 106-b. Further, in the inactive position 140 the spacer 110-b is compressed (i.e., flattened and/or retracted towards its upper end) and positioned in an upper portion of the gap 136. In some cases, the spacer 110-b may be positioned below the condyle head 111 and/or temporomandibular joint (TMJ) of the skull. Upon transition 150 to the active position 145, in some examples, the spacer 110-b expands (e.g., in a downward direction) and fills up a larger portion of the gap 136 between the mastoid or the temporal bone and the mandible bone. The spacer 110-b may be similar or substantially similar to the spacer 110-a described in relation to FIG. 1.

In some embodiments, the spacer 110 (e.g., spacer 110-a, spacer 110-b) may comprise a hard, rigid, and/or stiff material (e.g., surgical grade metal). In other embodiments, the spacer 110 may comprise a soft, flexible, and/or elastic material, such as foam, or other synthetic bio-compatible material. In one embodiment, the spacer 110 may be designed to be partially (or fully) compressed in the inactive position and return to its original shape (i.e., uncompressed state) in the active position, which allows the spacer 110 to fill up any additional gap or space between the mandible bone and the mastoid/temporal bones, as illustrated in FIG. 1B. In some examples, the spacer 110 may have a non-linear "spring constant" or k-value, such that a higher compression force is needed to deform/compress the spacer when it is in the uncompressed state as compared to a partially compressed state, or vice versa. In other cases, the spacer 110 may be an example of an inflatable member that is inflated when in the active position 145 and at least partially deflated in the inactive position 140. In such cases, the activation mechanism 170 may be used to inflate the spacer 110, where the activation mechanism 170 may comprise an air/fluid pump.

Figure 6:
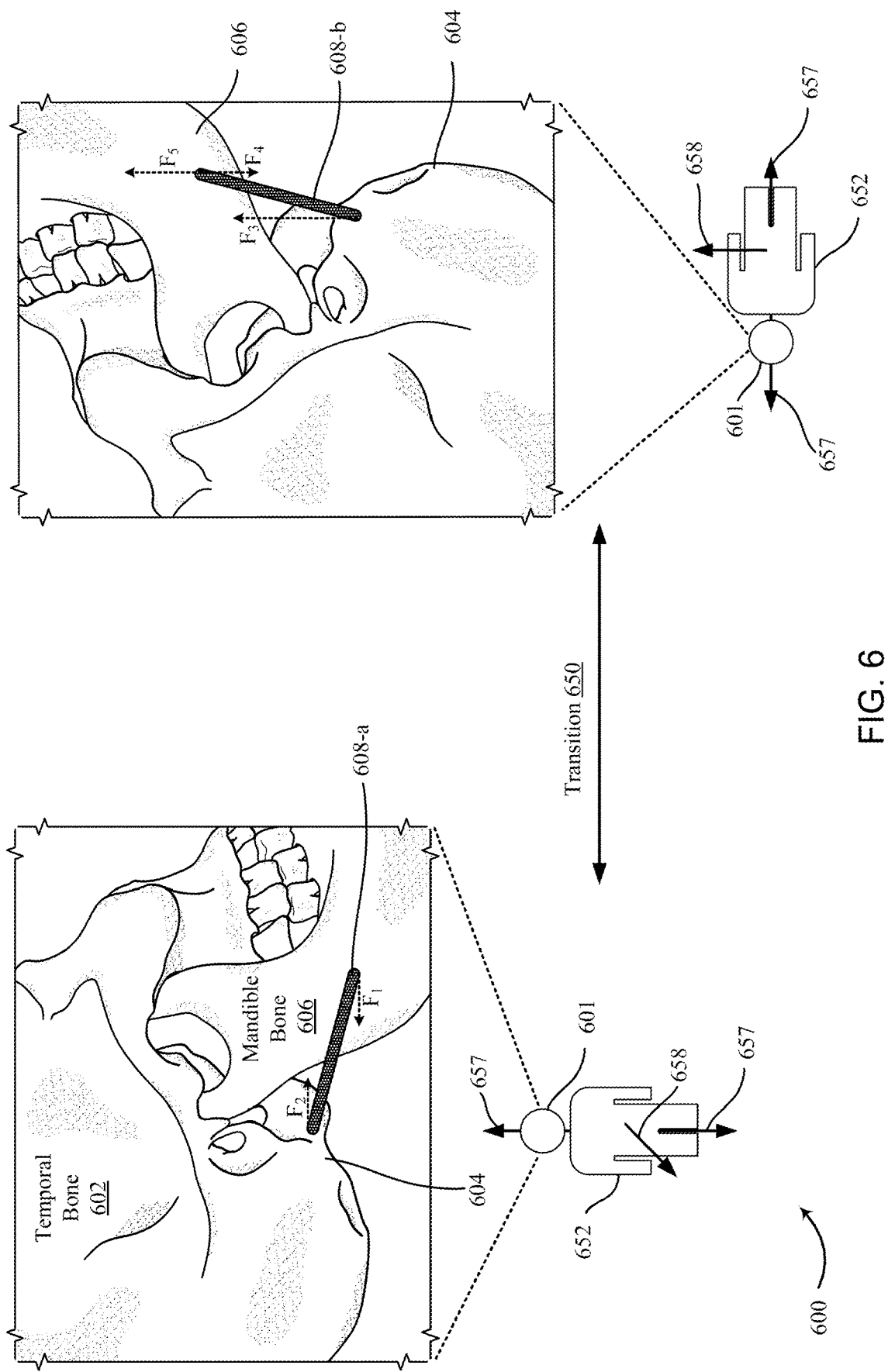
FIG. 6 depicts a process flow of an implant device being activated, according to various aspects of the disclosure.

In some cases, the activation mechanism 170 of the apparatus 100-a may move at least a portion of one or more of the implant (i.e., spacer 110-a), the first pivot device 120, and the second pivot device 122, such as during transition (e.g., transition 150 in FIG. 1B) between the inactive position and the active position, and vice versa. When a longitudinal axis 152 of the spacer 110-a is in a generally vertical position, the spacer 110-a may comprise a spacer 110-a in an active position. Such a vertical position of the longitudinal axis 152 may occur when the patient is in a horizontal or substantially horizontal position (e.g., patient is lying down or sleeping, as illustrated in FIG. 6; patient leans back by an angle exceeding a threshold, e.g., >135 degrees, >150 degrees, etc., in which case the angle 153 also increases). In some examples, changing a position, for instance, by increasing the angle 153, of the longitudinal axis 152 between a generally horizontal position (i.e., implant or spacer is in inactive position) and a generally vertical position (i.e., implant or spacer is in active position) is based at least in part on changing a position of the patient's skull 101. As seen, FIG. 1A shows a detailed view 189 of the angle 153 between the longitudinal axis 152 of the implant and a horizontal axis 158 passing through the patient.

Aspects of the present disclosure facilitate allaying upper airway obstructive breathing associated with sleep, such as, but not limited to sleep disordered breathing, sleep apnea, and snoring. For example, as the mandible bone 106 may be susceptible to retrodisplacement when a patient lays down, or leans back (e.g., in a reclining chair or seat), this movement may cause the mandible bone 106 (i.e., lower jaw) to settle in a posterior position, i.e., relative to when the patient is in a vertical or substantially vertical position. Posterior displacement of the mandible bone tends to be more pronounced during the deepest phases of sleep (e.g., Rapid Eye Movement (REM) sleep cycle) when the brain waves slow down, and the body's muscles are relaxed. The soft tissues at the base of the tongue and/or throat are at a greater risk of collapse and obstruction during this phase of sleep, which may lead to sleep disordered breathing, snoring, and/or sleep apnea. When implanted (e.g., surgically), the apparatus 100 (e.g., apparatus 100-a, apparatus 100-b) of the present disclosure enables the mandible bone 106 to be maintained in a more neutral position (e.g., by preventing posterior displacement of the second end 124-b of the spacer 110-a relative to the first end 124-a via application of an anterior force 125 on the mandible bone 106-a), in accordance with one or more aspects of the disclosure. Additionally, or alternatively, the implant or spacer 110 facilitates positioning the second end of the implant anteriorly relative to the first end by application of the anterior force 125. In the active position, the anterior force 125 applied by the spacer 110 on the mandible bone 106 may be of equal or greater magnitude than a posterior force applied by the mandible 106, e.g., due to gravity when in the horizontal position and the relaxation of the tissue during sleep, as described in herein. The anterior force 125 may help maintain airway patency by helping keep the soft tissues at the base of the tongue and/or throat more patent, by preventing them from collapsing posteriorly, and/or by maintaining their more neutral position, and/or by displacing these soft tissues more anteriorly as a consequence of the anterior displacement of the mandible by the implant, thereby alleviating the symptoms and impact of upper airway obstructive breathing, providing snoring relief, enhancing quality of sleep, etc. In some examples, the spacer 110 may apply minimal (or no) anterior force 125, i.e., between the mastoid or temporal bone and the mandible bone in the inactive position/upon deactivation. Upon activation, the spacer 110, which may comprise an inflatable material, inflates or moves into position, which helps displace the mandible bone 106 anteriorly relative to the mastoid bone 104 or the temporal bone 102.

Figure 2B:
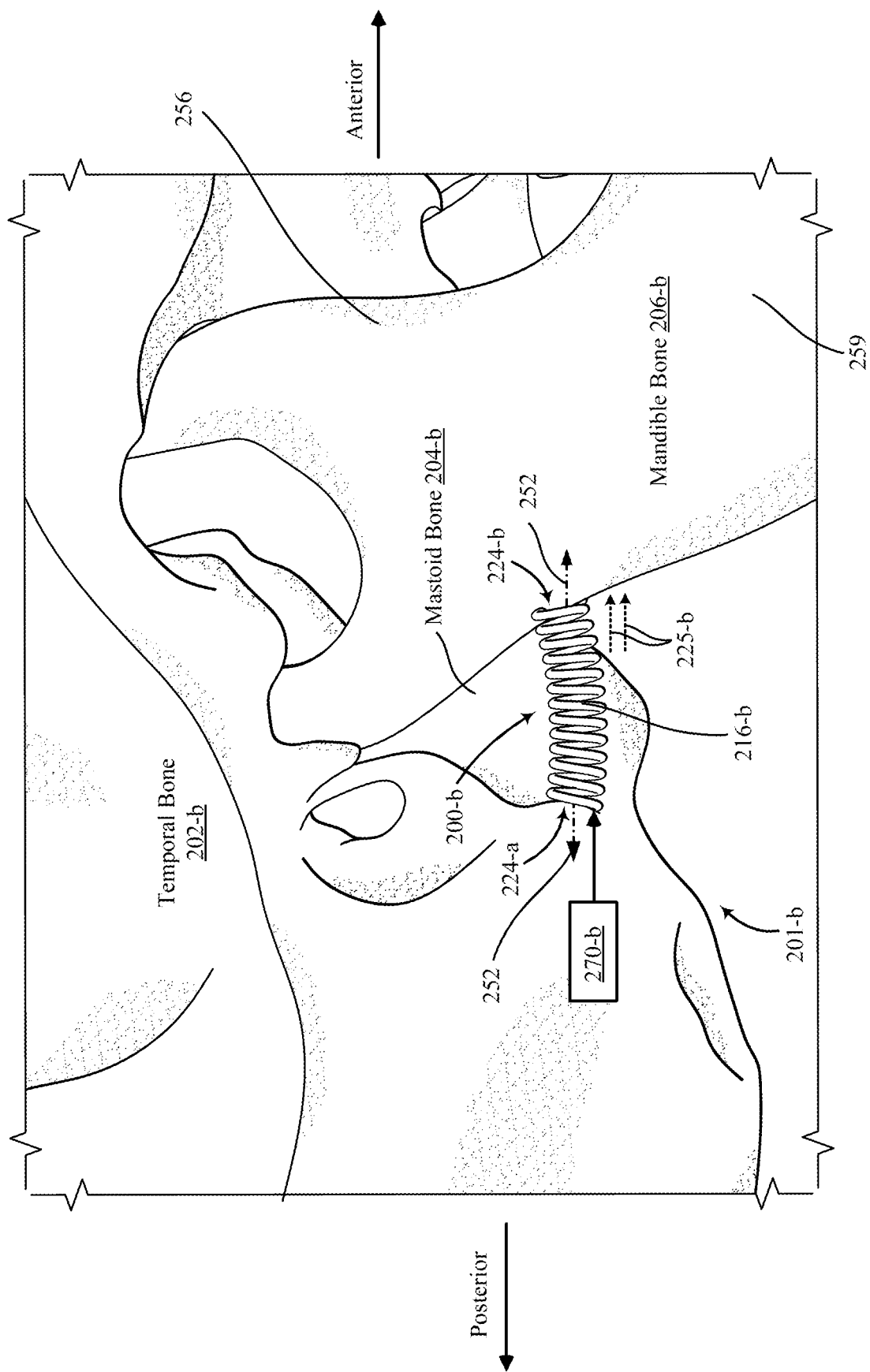
FIG. 2B illustrates a detailed view of the surgical implant device in FIG. 2A, according to various aspects of the disclosure.

Turning now to FIGS. 2A and 2B, which illustrate an apparatus 200 for relieving upper airway obstructive breathing and/or for providing snoring relief, in accordance with aspects of the present disclosure. Apparatus 200 implements one or more aspects of the apparatuses 100, 300, 400, and/or 800 described herein. The apparatus 200 (e.g., apparatus 200-a, apparatus 200-b) may be surgically implanted in or on bones of the patient's skull 201 (e.g., skull 201-a, skull 201-b), according to various aspects of the disclosure. As seen, the patient's skull 201 includes a temporal bone 202 (e.g., temporal bone 202-a, temporal bone 202-b), a mastoid bone 204 (e.g., mastoid bone 204-a, mastoid bone 204-b), and a mandible bone 206. In the example shown, the apparatus 200-a comprises a first pivot device 220 (e.g., first pivot device 220 in FIG. 2A) coupled to at least one of a mastoid bone 204 and/or a temporal bone 202 of the patient. Further, the apparatus 200 comprises a second pivot device (e.g., second pivot device 222 in FIG. 2A) coupled to a mandible bone 206 of the patient. The apparatus also includes an implant (e.g., spring 216-a, spring 216-b) positioned between the first pivot device 220 and the second pivot device 222, where a first end 224-a of the spring 216-b is coupled to the first pivot device (e.g., first pivot device 220 in FIG. 2A) and a second end 224-b of the spring 216-b is coupled to the second pivot device (e.g., second pivot device 222 in FIG. 2A). For example, the springs 216-a and 216-b may be anchored on one of the mastoid bone 204 or the temporal bone 202 using any of the anchoring mechanisms described throughout this disclosure or known throughout the art. In one non-limiting example, the anchoring mechanism may comprise a spring anchor (also referred to as a spring connector stud), which refers to a type of fastener for connecting springs to a body or a surface (e.g., bones). The spring anchor may comprise a head (e.g., with a drilled hole) at one end and a threaded body on the other end, where the threaded body is anchored to a bone and the spring 216 is looped or wrapped around the drilled hole. In some aspects of the present disclosure, a spring anchor (i.e., first pivot device 220, second pivot device 222) may be anchored on each of the mastoid (or temporal) bone and the mandible bone. Further, a first end 224-a of the spring 216 may be coupled to one of the spring anchors (e.g., first pivot device 220) and a second end 224-b of the spring 216 may be coupled to the other of the spring anchors (e.g., second pivot device 222).

When in the active position, the spring 216 facilitates positioning the second end 224-b of the spring 216 anteriorly relative to the first end 224-a by application of a generally anterior-directed force, where the anterior-directed force may be applied in the direction shown by arrows 225 (e.g., arrows 225-a in FIG. 2A, arrows 225-b in FIG. 2B). Further, the anterior force serves to prevent posterior displacement of the second end 224-b relative to the first end 224-a. The anterior force helps maintain airway patency by helping keep the soft tissues at the base of the tongue and/or throat more patent, thereby alleviating the symptoms and impact of upper airway obstructive breathing, providing snoring relief, enhancing quality of sleep, etc. As seen in FIG. 2B, the spring 216-b comprises a longitudinal axis 252 extending from the first end 224-a to the second end 224-b. In some cases, an activation mechanism 270 (e.g., activation mechanism 270-a in FIG. 2A, activation mechanism 270-b in FIG. 2B) coupled to the spring 216 activates the spring, causing it to extend when in the active position. This activation may be based in part on a change in a position of the longitudinal axis 252 between a generally horizontal position and a generally vertical position, for instance, due to a change in a position of the patient's skull 201 (e.g., skull 201-a, skull 201-b). The activation mechanism 270-b may move at least a portion of one or more of the spring 216-b, the first pivot device 220-a, and the second pivot device 222-a. An activation mechanism may also comprise a change in a position of the patient's jaw or may comprise a manual/pressure activation mechanism whereby a person may assert pressure to a portion of the implant to change the implant between the active and inactive position, and vice versa. In some cases, the activation mechanism 270-b may comprise one of a magnetic and an electromagnetic device. This activation may occur by use of an internal magnet, such as magnet 203 in FIG. 2A. Such a magnet (e.g., magnet 203) may be built into the spring, implant, or in a different location within the patient (e.g., near a top of a person's skull 201-a) and electrically connected to the implant and/or the activation mechanism 270 (e.g., activation mechanism 270-a in FIG. 2A) via one or more wires 283. An external magnet 263 may be applied or passed over/near the internal magnet 203 by the patient to activate or deactivate the magnet 203 and change the implant between active/inactive positions. It is further contemplated that the external magnet 263 may be placed on the overlying skin and held in place by magnetic force 274 to keep the implant engaged while it is attached to the skin and magnet activated. In some cases, deactivation may comprise removing the external magnet 263 from the skin to change the device from an active to an inactive position. In some other cases, the magnetic device (e.g., internal magnet 203) could be placed on the mastoid end/attachment of the spring 216, the mandibular end/attachment of the spring 216, or even along the length of the spring 216. In one non-limiting example, the spring 216 positioned between the first and the second pivot devices may be compressed (i.e., spring-loaded) when in the inactive position. Further, the spring 216 may extend/expand when the patient moves from a vertical (or substantially vertical position) to a horizontal (or generally horizontal position). In some cases, the spring 216 may be surgically implanted in an expanded/extended configuration and when the patient is in a horizontal position. In this way, the spring 216 moves between a spring-loaded or compressed configuration when the patient is in the vertical position to an expanded configuration when the patient is in the horizontal position. In some cases, the spring 216 comprises a non-linear load or a non-linear k-value. For instance, the spring 216 may be an example of a conical/tapered spring, a barrel compression spring (e.g., convex or concave spring), and a dual pitch spring, to name a few non-limiting examples. In yet other cases, the spring 216 may be inflated via the activation mechanism 270. In such cases, the spring 216 may comprise a first rigidity or a first stiffness in the active position and a second rigidity (or second stiffness) in the inactive position, where the second rigidity/stiffness is lower than the first rigidity. In this way, the spring 216 may be prevented from collapsing (or compressing) in the active position.

The spring 216 may apply one of a first biasing force and a zero-biasing force on the mandible bone 206 (or lower jaw) when in the inactive position. Further, in the active position, the spring 216 may apply a second biasing force on the mandible bone 206, where the second biasing force comprises a force that is at least one of greater than the first biasing force and along a different direction than a direction associated with the first biasing force. For example, the spring 216 may apply a first biasing force that is in a generally horizontal direction (e.g., in the same general direction as the anterior force 225-a seen in FIG. 2A) when in the inactive position and the anterior and posterior positions are generally parallel to the ground. Further, in the active position, the spring 216 may apply a second biasing force that is in a generally vertical direction (e.g., when the anterior and posterior directions are in the generally vertical directions due to a repositioning of the skull 201-a). In such an embodiment, the anterior direction may comprise an "up" direction away from the ground and the posterior direction may comprise a "down" direction towards the ground.

FIG. 3 illustrates an apparatus 300 for relieving upper airway obstructive breathing and/or for providing snoring relief, in accordance with aspects of the present disclosure. Apparatus 300 implements one or more aspects of the apparatuses 100, 200, and/or 400 described herein. The apparatus 300 may be surgically implanted in or on bones of the patient's skull 301, according to various aspects of the disclosure. As seen, the patient's skull 301 includes a temporal bone 302, a mastoid bone 304, and a mandible bone 306. In the example shown, the apparatus 300 comprises a first pivot device 320 coupled to at least one of a mastoid bone 304 and a temporal bone 302. Further, the apparatus 300 comprises a second pivot device 322 coupled to a mandible bone 306. The apparatus also includes an implant device, such as a post 312, coupled to the first pivot device 320 and the second pivot device 322, where a first end 324-a of the post 312 is coupled to the first pivot device 320 and a second end 324-b of the post 312 is coupled to the second pivot device 322. It should be noted that the post 312 may be coupled on one of the mastoid bone 304 or the temporal bone 302 using any of the coupling mechanisms described throughout this disclosure, such as, but not limited to, bone screws 368 or fasteners, plates 375-a and 375-b, and pins, or adhesives.

In some cases, the post 312 comprises an inactive position, where the inactive position enables posterior displacement of the second end 324-b relative to the first end 324-a, and an active position, where the active position may prevent posterior displacement of the second end 324-b relative to the first end 324-a and/or may position the second end 324-b of the post 312 anteriorly relative to the first end 324-a. When in the active position, the second end 324-b of the post 312 comprises an anterior position relative to the first end 324-a by application of an anterior force. One such anterior force may comprise a force applied in the direction shown by arrows 325. The anterior force helps maintain airway patency by helping to open the soft tissues at the base of the tongue and/or throat, thereby alleviating the symptoms and impact of upper airway obstructive breathing, providing snoring relief, enhancing quality of sleep, etc. The post 312 comprises a longitudinal axis 352 extending from the first end 324-a to the second end 324-b.

In some cases, an activation mechanism 370 coupled to the post 312 causes the post 312 to extend (e.g., lengthen along the longitudinal axis 352) when in the active position. This extension may be based in part on a change in a position of the longitudinal axis 352 between a generally horizontal position and a generally vertical position. The activation mechanism may move at least a portion of one or more of the post 312, the first pivot device 320, and the second pivot device 322. In some cases, the activation mechanism may comprise one of a magnetic and an electromagnetic device. In one non-limiting example, the post 312 may further comprise a non-linear load or a non-linear k-value. Further, the post 312 may extend/expand when the patient moves from a vertical (or substantially vertical) position to a horizontal (or generally horizontal) position, and retract when returning to a prior position. It is also contemplated that any other activation mechanism (i.e., one or more of magnetic, external pressure applied by the patient, jaw position, mechanical) disclosed herein may be used to extend/expand the post 312. It is contemplated that the post 312 may apply one of a first biasing force and a zero-biasing force on the mandible bone 306 (or lower jaw) when in the inactive position. Further, in the active position, the post 312 may apply a second biasing force on the mandible bone 306, where the second biasing force comprises a force that is at least one of greater than the first biasing force and along a different direction than a direction associated with the first biasing force. For example, the post 312 may apply a first biasing force that is in a generally horizontal direction (e.g., generally parallel to the floor or ground) when in the inactive position. Further, in the active position (e.g., when the anterior direction of a patient's skull 302 is generally upwards and the posterior direction of the patient's skull 302 is generally downwards), the post 312 may apply a second biasing force that is in a generally vertical direction (e.g., generally perpendicular to the floor or ground).

In some cases, the post 312 may comprise a telescoping design with two or more concentric tubes that can extend and increase the overall length of the post 312 (with the length extending between the first pivot device 320 and second pivot device 322). The concentric tubes of the post 312 may have the same or similar length. Further, the post 312 may comprise a collapsed orientation (i.e., length of post 312 is at a minimum) when in the inactive position and an expanded orientation (i.e., length of post 312 is greater than the minimum) when in the active position. The post 312 may transition between the collapsed orientation and the expanded orientation, and vice-versa, based on one of a mechanical or a magnetic activation. In some cases, the activation mechanism 370 may comprise one of a magnetic and an electromagnetic device. This activation could occur by use of an internal magnet (e.g., shown as internal magnet 203 in FIG. 2A) and an external magnet (e.g., shown as external magnet 263 in FIG. 2A) as described herein. One mechanical activation may be automatically triggered when an angle (e.g., angle 353) between the post 312 and an axis (e.g., transverse axis 356, longitudinal axis, shown as longitudinal axis 657 in FIG. 6) passing through the patient exceeds a threshold angle. As seen, FIG. 3 shows a detailed view 389 of the angle 353 between the longitudinal axis 352 of the implant and a horizontal axis 358 passing through the patient. Alternatively, the mechanical activation may be manually triggered by action of the patient/user. In one non-limiting example, a patient may mechanically activate/deactivate the post 312 by moving their jaw, thereby causing the post 312 to transition between the inactive position and the active position, and vice versa. The patient may activate the implant by protruding their jaw forward, or in another position, and/or by applying an external pressure on the implant with a finger pressing on the implant while maintaining the jaw in a certain position, as further described in relation to FIGS. 7A and 7B below. The implant could then be deactivated in a similar fashion by again moving the jaw into a certain position and then again applying external pressure on the implant using a finger, for instance.

Figure 7B:
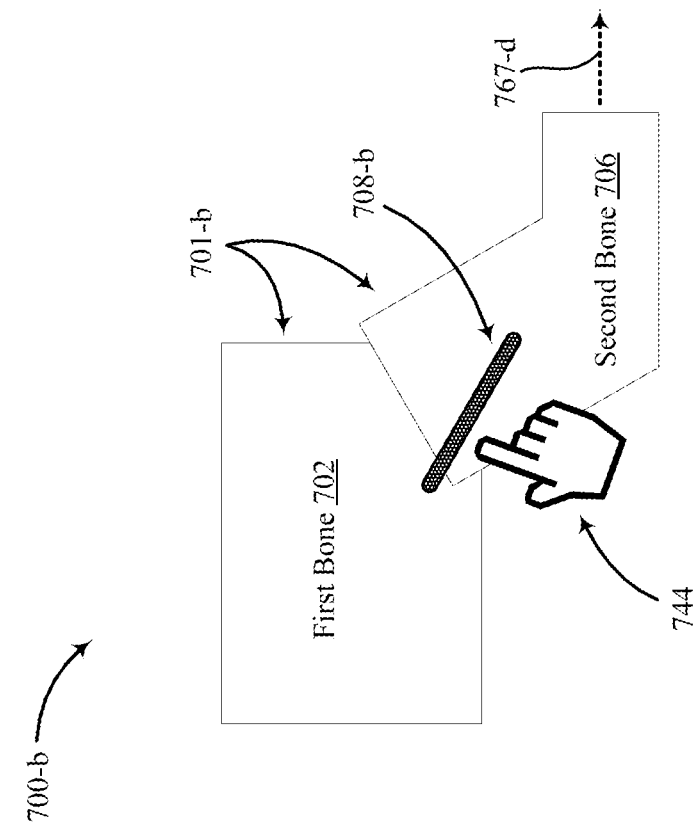
FIGS. 7A and 7B illustrate schematic diagrams of surgical implants transitioning between an inactive position and an active position based on user action, according to various aspects of the disclosure.
Figure 7A:
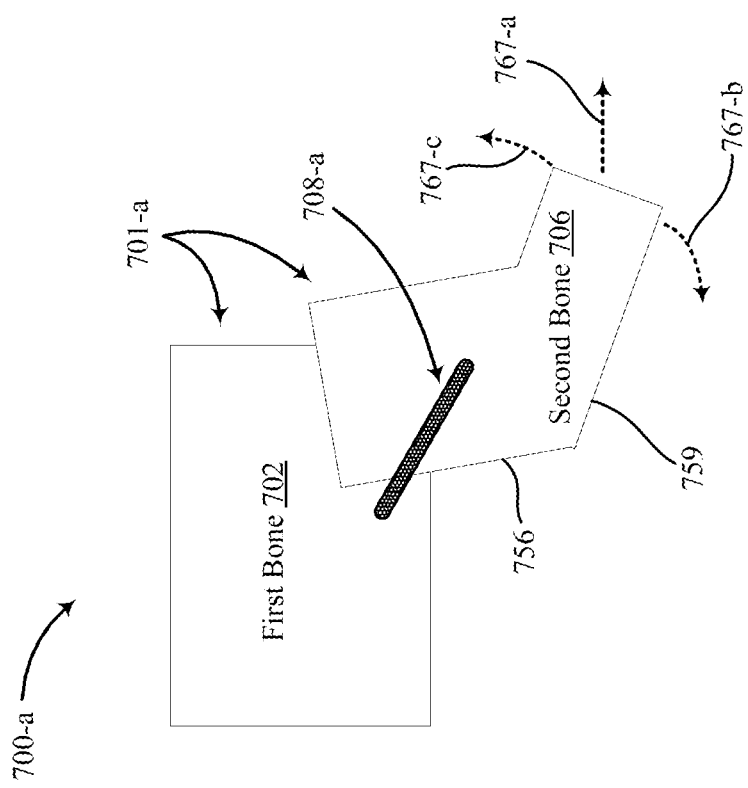

Turning now to FIGS. 7A and 7B, which illustrate schematic diagrams 700-a and 700-b, respectively, of surgical implants being activated (or deactivated) based on user action, in accordance with various aspects of the disclosure. As seen in FIG. 7A, an implant 708 is surgically implanted on a first bone 702 and a second bone 706 of a patient's skull 701-a. The first bone 702 may be one of the mastoid or the temporal bone, while the second bone 706 may be the mandible/lower jaw-bone. The second bone 706 comprises a plurality of sections, including a ramus 756 and a body 759, where the ramus 756 and body 759 intersect at an angle, as illustrated in FIGS. 7A and 7B. In accordance with aspects of the disclosure, the implant 708 may be anchored anywhere along the ramus 756 or the body 759 of the second bone 706 (i.e., mandible bone). In some cases, the patient may activate the implant 708 by moving their jaw (e.g., lower jaw) in a certain manner (e.g., in a direction associated with one or more of arrows 767-a, 767-b, and/or 767-c). For instance, the patient may move their jaw or second bone 706 forward (e.g., as shown by arrow 767-a), up (e.g., as shown by arrow 767-c), down (e.g., as shown by arrow 767-b), along an arc (e.g., as shown by arrows 767-b and 767-c), or in another position to activate the implant 708. To deactivate the implant, the patient may move their jaw or second bone 706 in an opposite direction or manner to that used to activate the implant. Alternatively, the patient may move their jaw or second bone 706 to the same position or in the same direction as the one used to activate the implant.

FIG. 7B illustrates another example of mechanical activation of an implant 708-b based on user action, in accordance with various aspects of the disclosure. In this example, the implant 708-b is activated by applying an external pressure, for instance, using fingers 744 pressing on the implant 708-b. In some instances, the jaw or second bone 706 may also be maintained in a certain position (e.g., forward position, as shown by arrow 767-d) to activate the implant 708. Furthermore, to deactivate the implant, the patient may apply external pressure on the implant (e.g., using fingers 744) and move their jaw (e.g., to a rearward position opposite in direction to arrow 767-d), in one non-limiting example.

It should be noted that, the mechanical activation/deactivation described in relation to FIGS. 7A and 7B may be applicable to any of the surgical implants/apparatuses described herein, such as, but not limited to, the spacer 110, spring 216, post 312, chain 414, and/or hinged post 879.

Returning to FIG. 3, in another example, the activation mechanism comprises a piston 371 (e.g., air piston, foam piston), a piston rod 372, and/or an air/fluid pump and reservoir 373. In some cases, one or more components (e.g., piston 371, piston rod 372, and/or air/fluid pump and reservoir 373) of the activation mechanism 370 may be optional, as indicated by the dashed lines. In some cases, the air/fluid pump and reservoir 373 compresses air (or another fluid) that expands and exerts a force on the piston 371 and piston rod 372. In some embodiments, the air/fluid pump and reservoir 373 comprises a reservoir filled with air/ another fluid and a manual pump, where the pump may be activated by the patient/user. For instance, the user or patient may depress an area (e.g., on the side of the face or jaw, as shown in FIG. 7B, adjacent or behind the ear, etc.) of their body to insert/remove the air/fluid to the piston. The piston assembly comprising the piston 371 and piston rod 372 may be used to transfer the force from the expanding air/fluid to the post 312, for instance, to activate the post 312. In some cases, the force exerted by the piston and/piston rod may be in the same or similar direction, have the same or a similar magnitude, or a combination thereof, as the second biasing force. In some examples, for instance, if the post 312 comprises a telescoping design, the piston assembly may exert a force (i.e., along the longitudinal axis of the post 312) that enables the post 312 to extend in length, which allows the post 312 to apply an anterior force on the mandible bone 306. It should be noted that, other mechanical activation techniques are contemplated in different embodiments, and the examples listed herein are not intended to be limiting.

In some examples, magnetic activation may be utilized to transition the post 312 between the inactive and the active position, and vice versa. In some cases, magnetic activation may be triggered based on a magnetic field strength at or near a first magnetic device coupled to the post 312 exceeding a threshold magnetic field strength, where the magnetic field strength is generated by a second magnetic device. This magnetic device could be placed on the mastoid end/attachment of the post implant, or the mandibular end/attachment of the implant, or along the length of the post of the implant. For example, the magnetic activation may comprise two magnets arranged such that their repelling poles (e.g., North poles, South poles) are facing each other. In the inactive position, the magnets may be positioned sufficiently apart such that the magnetic field strength or repelling force between the magnets is below a threshold. Further, when the longitudinal axis 352 of the post 312 changes between a generally horizontal position and a generally vertical position, the distance between the magnet's changes (e.g., becomes smaller), increasing the repelling force or magnetic field strength between the magnets. In some cases, if the magnetic field strength or repelling force (e.g., shown as magnetic force 274 in FIG. 2A) exceeds a threshold, the post 312 transitions into the active position, where it may remain until deactivation, and uncoupling of the magnetic forces occurs. In some cases, the post 312 transitions into the inactive position, for instance, when the magnetic field strength or repelling force falls below the threshold. In yet other cases, magnetic activation may be implemented using a first magnet (e.g., at or near the implant, positioned internal to the patient) and a second magnet (e.g., an external magnet), where the patient moves the second magnet around the sides of the face to activate the first magnet and transition the post 312 to the active position. Other magnetic activation techniques are contemplated, and the examples listed herein are not intended to be limiting.

FIG. 4 illustrate an apparatus 400 for relieving upper airway obstructive breathing and/or for providing snoring relief, in accordance with aspects of the present disclosure. Apparatus 400 implements one or more aspects of the apparatuses 100, 200, and/or 300 described herein. The apparatus 400 may be surgically implanted in or on bones of the patient's skull 401, according to various aspects of the disclosure. As seen, the patient's skull 401 includes a temporal bone 402, a mastoid bone 404, and a mandible bone 406. In the example shown, the apparatus 400 comprises a first pivot device 420 anchored to at least one of a mastoid bone 404 and a temporal bone 402 of the patient. In other cases, the first pivot 420 may be anchored at a location between the mastoid bone 404 and the temporal bone 402. Further, the apparatus 400 comprises a second pivot device 422 anchored to a mandible bone 406 of the patient. The apparatus also includes an implant, such as a chain 414, positioned between the first pivot device 420 and the second pivot device 422, where a first end 424-a of the chain 414 is coupled to the first pivot device 420 and a second end 424-b of the chain 414 is coupled to the second pivot device 422. It should be noted that, the chain 414 may be anchored on one of the mastoid bone 404 or the temporal bone 402 using any of the anchoring mechanisms described throughout this disclosure.

In some cases, the chain 414 comprises an inactive position, where the inactive position enables posterior displacement of the second end 424-b relative to the first end 424-a, and an active position, where the active position at least one of prevents posterior displacement of the second end 424-b relative to the first end 424-a and positions the second end 424-b of the chain 414 anteriorly relative to the first end 424-a. For instance, the chain 414 may facilitate positioning the second end 424-b of the chain 414 anteriorly relative to the first end 424-a by application of an anterior force, where the anterior force is applied in the direction shown by arrows 425. As noted above, this anterior force may help maintain airway patency by helping keep the soft tissues at the base of the tongue and/or throat more patent, thereby alleviating the symptoms and impact of upper airway obstructive breathing, providing snoring relief, enhancing quality of sleep, etc. The chain 414 may comprise a slack orientation in the inactive position and a taut orientation in the active position, where the taut orientation applies a biasing force that displaces the lower jaw (or mandible bone 406) anteriorly relative to the mastoid bone and/or the temporal bone. This biasing force may be applied on the second pivot device, for instance, when the chain is in the taut orientation.

In some cases, an activation mechanism 470 coupled to the chain 414 helps transition the chain 414 from the inactive position to the active position. In some examples, the chain 414 is inflatable (i.e., hollow or substantially hollow) and coupled to the activation mechanism 470. Further, the activation mechanism 470 may comprise an air/fluid pump and reservoir (e.g., shown as air/fluid pump and reservoir 373 in FIG. 3) that compresses air (or another fluid) and pushes it into the chain 414, i.e., during transition from the inactive position to the active position. This compressed air (or fluid) inflates the chain 414 and transforms the chain 414 from a slack orientation to a taut orientation. In the active position, the chain 414 may become more rigid/stiff and expand (e.g., in length and/or width). In this example, deactivation of the chain 414 may comprise deflating the chain 414 so it reverts to the slack orientation. In some other cases, the chain 414 may be composed of metal or other material known in the art. Further, at least one of the pivot devices (e.g., second pivot device 422) may comprise a sliding mechanism that slides the corresponding end (e.g., second end 424-b) of the chain between a first location (i.e., in the inactive position) to a second location (i.e., in the active position), where the second location is anterior relative to the first location. The sliding mechanism may be coupled to the chain 414 and the activation mechanism 470. One such activation mechanism 470 may comprise a piston, piston rod, and/or an air pump, where the piston rod is coupled to the sliding mechanism. In such cases, during activation, compressed air (i.e., from the air pump) may push the piston and piston rod such that the sliding mechanism and second end 424-b of the chain slide from the first location to the second location. Further, the sliding mechanism and/or second end 424-b of the chain may remain at the second location when the chain 414 is in the active position (e.g., when the patient is in a horizontal or substantially horizontal position) until deactivation. In some cases, the sliding mechanism and/or second end 424-b may unlock from the second location when the patient moves from a horizontal to a vertical position, which allows the second end 424-b of the chain 414 to slide (posteriorly) and return to the first location, thereby returning the chain 414 to a slack orientation.

In some examples, magnetic activation may be utilized to transition the chain 414 between the inactive and the active position, and vice versa. In some cases, magnetic activation may be triggered based on a magnetic field strength at or near a first magnetic device coupled to the chain 414 exceeding a threshold magnetic field strength, where the magnetic field strength is generated by a second magnetic device. This magnetic device could be placed on the mastoid end/attachment of the implant, or the mandibular end/attachment of the implant, or along the length of the chain 414. For example, the magnetic activation may comprise two magnets arranged such that their repelling poles (e.g., North poles, South poles) are facing each other. In the inactive position, the magnets may be positioned sufficiently apart such that the magnetic field strength or repelling force between the magnets is below a threshold. Further, when the position of the patient changes, e.g., between a generally vertical position and a generally horizontal position, the distance between the magnet's changes (e.g., becomes smaller), increasing the repelling force or magnetic field strength between the magnets. In some cases, if the magnetic field strength or repelling force exceeds a threshold, the chain 414 transitions into the active position, where it may remain until deactivation, and uncoupling of the magnetic forces occurs. In some cases, the chain 414 transitions into the inactive position, for instance, when the magnetic field strength or repelling force falls below the threshold. In yet other cases, magnetic activation may be implemented using a first magnet (e.g., at or near the implant, positioned internal to the patient, such as internal magnet 203 in FIG. 2A) and a second magnet (e.g., an external magnet, such as external magnet 263 in FIG. 2A), where the patient moves the second magnet around the sides of his/her face to activate (e.g., via magnetic force 274) the first magnet and transition the chain 414 to the active position. Other magnetic activation techniques are contemplated, and the examples listed herein are not intended to be limiting. In yet other cases, the chain 414 may transition between the active and inactive positions (and vice-versa) based on an external pressure applied by the patient on/near the implant or based on movement of the mandible bone 406.

In some cases, an implant (e.g., implant 608, implant 708) comprising two sections (e.g., posts) connected using a hinge joint, or ball/pivot joint may be utilized, in accordance with one or more aspects of the disclosure, further described below in relation to FIG. 8. For instance, the hinge (e.g., joint 893) may be positioned between the first end 824-a of the implant or apparatus 800 and the second end 824-b of the apparatus 800, where one of the sections (e.g., post 814-a) may extend between the first end 824-a and the hinge and the other of the sections (e.g., post 814-b) may extend between the second end 824-b and the hinge. The apparatus 800 may be shaped and sized such that the combined length of the two sections (or posts 814) is slightly longer than the distance between the first and second pivot devices 820 and 822, respectively. In the inactive position, the apparatus 800 comprises a slack orientation such that the posts 814 are at an angle with respect to the hinge or joint 893. Upon activation (e.g., via the activation mechanism 870), the apparatus 800 transitions to a straight orientation such that the posts 814 and the hinge are generally aligned (e.g., at about 180 degrees) and remain in position until deactivation. In this way, the apparatus 800 prevents upper airway obstruction by maintaining the mandible bone 806 in a neutral and/or an anterior position when the patient is asleep, reclined backwards, etc.

FIG. 8 illustrate an apparatus 800 for relieving upper airway obstructive breathing and/or for providing snoring relief, in accordance with aspects of the present disclosure. Apparatus 400 implements one or more aspects of the apparatuses 100, 200, 300, and/or 400 described herein. The apparatus 800 may be surgically implanted in or on bones of the patient's skull 801, according to various aspects of the disclosure. As seen, the patient's skull 801 includes a temporal bone 802, a mastoid bone 804, and a mandible bone 806. In the example shown, the apparatus 800 comprises a first pivot device 820 anchored to at least one of a mastoid bone 804 and a temporal bone 802 of the patient. In other cases, the first pivot 820 may be anchored at a location between the mastoid bone 804 and the temporal bone 802. Further, the apparatus 800 comprises a second pivot device 822 anchored to a mandible bone 806 of the patient. The apparatus also includes an implant, such as a hinged post 879, positioned between the first pivot device 820 and the second pivot device 822, where a first end 824-a of the hinged post 879 is coupled to the first pivot device 820 and a second end 824-b of the hinged post 879 is coupled to the second pivot device 822. Further, the hinged post 879 comprises a first post 814-a, a joint 893 (e.g., a hinge joint or a ball/pivot joint), and a second post 814-b, where the joint 893 is connected to each of the first and the second posts 814. It should be noted that, the hinged post 879 may be anchored on the mandible bone 806 and one of the mastoid bone 804 or the temporal bone 802 using any of the anchoring mechanisms described throughout this disclosure, such as, but not limited to, bone plates 875-a and 875-b, and one or more screws 868 (e.g., surgical or bone screws).

In some cases, the hinged post 879 comprises an inactive position, where the inactive position enables posterior displacement of the second end 824-b relative to the first end 824-a, and an active position, where the active position at least one of prevents posterior displacement of the second end 824-b relative to the first end 824-a and positions the second end 824-b of the hinged post 879 anteriorly relative to the first end 824-a. For instance, the hinged post 879 may facilitate positioning the second end 824-b of the hinged post 879 anteriorly relative to the first end 824-a by application of an anterior force, where the anterior force is applied in the direction shown by arrows 825. As noted above, this anterior force may help maintain airway patency by helping keep the soft tissues at the base of the tongue and/or throat more patent, thereby alleviating the symptoms and impact of upper airway obstructive breathing, providing snoring relief, enhancing quality of sleep, etc. The hinged post 879 may comprise a bent or slack orientation in the inactive position and a taut or unbent orientation in the active position, where the taut orientation applies a biasing force that displaces the lower jaw (or mandible bone 806) anteriorly relative to the mastoid bone and/or the temporal bone. This biasing force may be applied on the second pivot device, for instance, when the hinged post 879 is in the taut orientation. In some cases, the joint 893 (e.g., hinge joint) may be positioned in a recess or channel 869 and may be movable within the channel 869 as the hinged post transitions between the inactive and active position, and vice-versa. FIG. 8 depicts the hinged post 879 in both the active (i.e., hinged post 879 is unbent/straight and shown in light-dotted shading) and inactive (i.e., hinged post 879 is bent and shown in dark-dotted shading) positions. In this example, during transition from the inactive to the active position, the joint 893 may slide downward within the channel or recess 869, as shown by arrows 862, so that the first post 814-a, the second post 814-b, and the joint 893 are generally aligned.

In some cases, an activation mechanism 870 coupled to the hinged post 879 helps transition the hinged post 879 from the inactive position to the active position. In some examples, the hinged post 879 is inflatable (i.e., hollow or substantially hollow) and coupled to the activation mechanism 870. Further, the activation mechanism 870 may comprise an air/fluid pump and reservoir (e.g., shown as air/fluid pump and reservoir 373 in FIG. 3) that stores air (or another fluid) in a reservoir, where the reservoir is coupled to a pump. The pump draws the air/fluid stored in the reservoir, compresses it, and pushes it into the hinged post 879, i.e., during transition from the inactive position to the active position. This compressed air (or fluid) inflates the first and the second posts 814 causing the first and the second posts 814 to exert a downward pressure/force (as shown by arrows 862) on the joint 893. In some cases, the joint 893 may lock into place at the bottom end of the recess/channel 869. In this way, the activation mechanism 870 transforms the hinged post 879 from a slack/bent orientation to a taut/straight orientation. In the active position, the hinged post 879 may become more rigid/stiff and expand (e.g., in length and/or width). In some other cases, the first and/or the second posts 814 of the hinged post 879 may be composed of metal or other material known in the art. Additionally, or alternatively, the activation mechanism 870 may comprise a piston, piston rod, and/or an air pump, where the piston rod is coupled to the sliding joint (e.g., joint 893 in recess/channel 869). In such cases, during activation, compressed air (i.e., from the air pump) may push the piston and piston rod such that the joint 893 slides from the top end to the bottom end of the channel/recess 869 (i.e., shown by hinged post 879 in light-dotted shading). Further, the joint 893 may remain at this location (e.g., bottom end of channel/recess 869) when the hinged post 879 is in the active position (e.g., when the patient is in a horizontal or substantially horizontal position) until deactivation. In some cases, the joint 893 may unlock from this location when the patient moves from a horizontal to a vertical position, allowing it to slide (upward) and return to the inactive location, thereby returning the hinged post 879 to a slack/bent orientation (i.e., as shown by hinged post 879 in dark-dotted shading).

In some examples, magnetic activation may be utilized to transition the hinged post 879 between the inactive and the active position, and vice versa. In some cases, magnetic activation may be triggered based on a magnetic field strength at or near a first magnetic device coupled to the hinged post 879 exceeding a threshold magnetic field strength, where the magnetic field strength is generated by a second magnetic device. This magnetic device could be placed on the mastoid end/attachment of the implant, or the mandibular end/attachment of the implant, or along the length of the hinged post 879. In some cases, if the magnetic field strength or repelling force exceeds a threshold, the hinged post 879 transitions into the active position, where it may remain until deactivation, and uncoupling of the magnetic forces occurs. In some cases, the hinged post 879 transitions into the inactive position, for instance, when the magnetic field strength or repelling force falls below the threshold. In yet other cases, magnetic activation may be implemented using a first magnet (e.g., at or near the implant, positioned internal to the patient, such as internal magnet 203 in FIG. 2A) and a second magnet (e.g., an external magnet, such as external magnet 263 in FIG. 2A), where the patient moves the second magnet around the sides of his/her face to activate (e.g., via magnetic force 274) the first magnet and transition the hinged post 879 to the active position. In another example, the joint 893 may be magnetic and the user/patient may change the location of the joint 893 using an external magnet (e.g., active the implant by moving the external magnet in a first direction, deactivate the implant by moving the external magnet in a second, different direction). Other magnetic activation techniques are contemplated, and the examples listed herein are not intended to be limiting.

Figure 5:
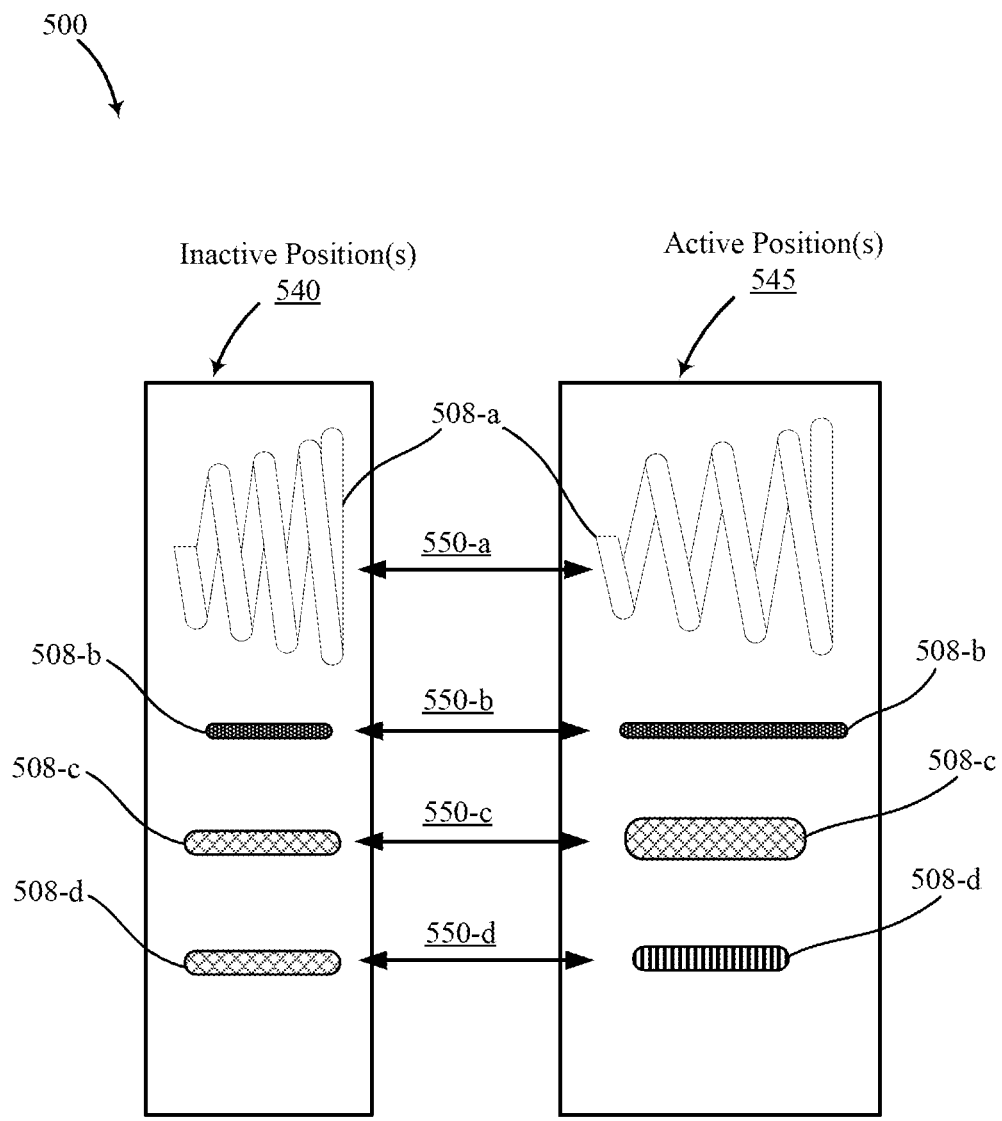
FIG. 5 depicts an illustration of various surgical implant device(s) transitioning between an inactive position and an active position, according to various aspects of the disclosure.

FIG. 5 depicts an illustration 500 of various implant device(s) 508 transitioning between an inactive position 540 and an active position 545, according to various aspects of the disclosure. Arrows 550 represent the transition between the inactive position 540 and the active position 545 and vice-versa. As noted above, implant devices (e.g., chain 414, post 312, spring 216, spacer 110, hinged post 879) may be coupled to pivot devices (i.e., anchored to the bones of the patient's skull), and optionally, an activation mechanism (e.g., activation mechanisms 170, 270, 370, 470, and/or 870). Further, the activation mechanism may move at least a portion of one or more of the implant device 508 and the pivot device(s) during activation/deactivation of the implant device 508.

In some cases, a transition (e.g., shown by arrow 550-a) may expand an overall length of an implant 508-a (e.g., a spring, such as spring 216 in FIGS. 2A and B). In another example, a transition (e.g., shown by arrow 550-b) may expand an overall length of an implant 508-b, where the implant 508-b may be an example of the post 312 previously described in relation to FIG. 3 and/or the hinged post 879 described in relation to FIG. 8. The post 312 may be an example of a telescoping post comprising a plurality of concentric hollow tubular sections that are slidably received within each other. These hollow tubular sections may be interconnected, which may allow the implant 508-b to retract when in the inactive position 540 and extend when in the active position 545. In other cases, the implant 508-b may be an example of the chain 414, previously described in relation to FIG. 4. In either case, the extension of the implant 508-b may be based in part on a change in a position of a longitudinal axis (i.e., of the implant 508-b) between a generally horizontal position and a generally vertical position.

In some examples, an implant 508 (e.g., implant 508-c) may comprise an inflatable member, where the implant 508-c inflates in the active position 545 and at least partially deflates in the inactive position 540. Arrow 550-c depicts this transition of the implant 508-c between a partially deflated state and an inflated state, in accordance with various aspects of the disclosure. As depicted, the implant 508-c may comprise an increased length, an increased width, or a combination thereof, in the active position 545 as compared to the inactive position 540. Further, the implant 508-c may apply one of a first biasing force and a zero-biasing force on the mandible bone (or lower jaw) in the inactive position and a second biasing force on the mandible bone in the active position. The second biasing force may comprise a force that is at least one of greater than the first biasing force and along a different direction than a direction associated with the first biasing force. In some examples, the implant 508-c may be inflated using an air/fluid pump that forces compressed air (or another fluid) into the implant 508-c. The implant 508-c may comprise a first rigidity or a first stiffness when in the active position 545 and a second rigidity or a second stiffness when in the inactive position 540, where the first rigidity or first stiffness is greater than the second rigidity or second stiffness.

Arrow 550-d depicts a transition between an inactive position 540 and an active position 545 for an implant 508-d. In this example, the implant 508-d comprises a non-linear load or a non-linear k-value. For instance, the implant 508-d comprises a first load or first k-value in the inactive position and a second load or second k-value in the active position 545, where the first and second load/k-values are different (i.e., as depicted by the different shading for implant 508-d in the active and inactive positions). Alternatively, the implant 508-d comprises a first rigidity or a first stiffness in the active position 545 and a second rigidity or a second stiffness in the inactive position 540, where the first rigidity or first stiffness is greater than the second rigidity or second stiffness (e.g., as depicted by the different shading for implant 508-d in the active and inactive positions). In some cases, the implant 508-d comprises a non-linear spring, such as, but not limited to, a conical/tapered spring, a barrel compression spring (e.g., convex spring, concave spring), or a dual pitch compression spring. Alternatively, the implant 508-d comprises a spacer (e.g., shown as spacer 110 in FIG. 1) and/or an inflatable material. In some cases, the implant 508-d may be composed of a material that is elastic (e.g., like a foam earplug) that can transition from a soft compressed state in the inactive position 540 to a more rigid expanded state in the active position 545. The implant 508-d may only activate at certain angles (e.g., when the patient is in a horizontal or substantially horizontal position). In one non-limiting example, the implant 508-d may slide into a gap or space between the mastoid or temporal bone, and the mandible bone when activated. It is yet further contemplated that the active position 545 may comprise a similar or the same position as the inactive position 540 and is such cases, the stiffness of the material comprising the implant 508 may prevent a change in the length of the implant (e.g., a compression) due to a softening of the tissues in the throat, tongue, etc., and preventing snoring. In some cases, a sliding mechanism, such as the one described in relation to FIGS. 4, may be utilized with one or more of the other implants (e.g., post 312, hinged post 879) described herein. In one non-limiting example, a sliding mechanism may comprise an extension spring, where the extension spring may be coupled to one end (e.g., second end 824-b) of a post-hinge mechanism. In the inactive position, the extension spring applies a first or a zero pulling force on the second end of the hinged post 879, for instance, the anterior end of second post 814-b. Further, in the active position, the extension spring creates a resistance to prevent a downward pulling force (e.g., gravity) from pulling the second end 824-b of the hinged post 879 in a posterior direction. In this way, the extension spring, sliding mechanism, and hinged post 879 help maintain the mandible bone 806 in a neutral and/or an anterior position, which reduces the chances of upper airway obstruction and snoring.

FIG. 6 provides a pictorial representation of a process flow 600 for an implant device 608 transitioning (shown by transition arrow 650) between an inactive position (shown with forces $F_1$ and $F_2$) and an active position (shown with force Fs) and vice-versa, according to various aspects of the disclosure. For ease of reference, the implant device 608 is referred to as implant device 608-a in the inactive position and implant device 608-b in the active position. The implant device 608 may be similar or substantially similar to any of the implant devices described herein and elsewhere throughout the disclosure. For instance, the implant device 608 may implement one or more aspects of the spacer 110, spring 216, post 312, chain 414, hinged post 879, and/or implant devices 508, previously described in relation to FIGS. 1-5 and/or 8.

In some aspects of the present disclosure, the implant device 608 may be surgically implanted in a patient 652, for instance, for relieving upper airway obstructive breathing and/or for providing snoring relief. For example, the implant device 608 may be surgically implanted in or on bones (e.g., mandible bone 606, mastoid bone 604 and/or temporal bone 602) of the skull 601 using one or more pivot devices (also referred to as anchoring devices), as described and shown throughout the specification and figures. As used herein and elsewhere in the disclosure, the term "transverse axis" may refer to an axis passing through (e.g., from front to back) of the patient, while the term "longitudinal axis" may refer to an axis passing through (e.g., from head to toe) of the patient. In the example shown, the longitudinal axis passing through the patient 652 is shown as longitudinal axis 657 and the transverse axis as transverse axis 658. In the inactive position (e.g., when patient 601 is in a vertical position, such as while sitting or standing, in which case the longitudinal axis 657 passing through the patient is perpendicular to the ground), the implant device 608-a may apply a first biasing force (i.e., the combination of $F_1$ and $F_2$, or $F_2-F_1$), or alternatively, a zero-biasing force (e.g., if horizontal forces $F_2$ and Fi are equal) on the mandible bone 606. Further, in the active position (e.g., when patient 652 is sleeping, in which case the longitudinal axis 657 passing through the patient is parallel to the ground), the implant 608 applies a second biasing force on the mandible bone 606, where the second biasing force comprises a force that is at least one of greater than the first biasing force and along a different direction than a direction associated with the first biasing force. For example, the implant 608-a applies a first biasing force ($F_2-F_1$) that is in a generally horizontal direction (e.g., generally parallel to the floor or ground) when in the inactive position. Further, in the active position, the implant 608-b applies a second biasing force ($F_5$) that is in a generally vertical direction (e.g., generally perpendicular to the floor or ground). While not necessary, the first and/or second biasing forces may be applied on a pivot device anchored to the mandible bone (or lower jaw) of the patient. In the example shown, the second biasing force is based at least in part on a combination of an upward biasing force ($F_3$) and a downward biasing force ($F_4$). For instance, the second biasing force ($F_5$) represents the combination of the forces $F_3$ and $F_4$ and is in a generally vertical direction. In accordance with various aspects of the disclosure, this second biasing force or $F_5$ helps prevent the mandible bone 606 (or lower jaw) from shifting posteriorly and/or helps maintain the soft tissues at the base of the tongue, soft tissues in the throat, etc., from collapsing and obstructing the upper airway of the patient 652.

It should be noted that, the mandible (as shown in the figures) may be outsized or enlarged as compared to the mastoid or temporal bones to illustrate various aspects of the surgical implant(s) more clearly. Therefore, the relative distances/locations may not be as accurate, nor are they intended to limit the scope of this disclosure.

As used herein, the recitation of "at least one of A, B and C" is intended to mean "either A, B, C or any combination of A, B and C." The previous description of the disclosed embodiments is provided to enable any person skilled in the art to make or use the present disclosure. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. An apparatus for relieving upper airway obstructive breathing in a patient, the apparatus comprising:
   a first pivot device configured to anchor to at least one of a mastoid bone and a temporal bone of the patient:
   a second pivot device configured to anchor to a mandible bone of the patient:
   an implant positioned between the first pivot device and the second pivot device; and wherein the implant comprises,
      a first end of the implant configured to be coupled to the first pivot device,
      a second end of the implant configured to be coupled to the second pivot device,
      the implant comprising any of a spring, a cylindrical post, a chain, and a spacer;
      the implant configured to be disposed in an inactive position or an active position, the inactive position enabling a posterior displacement of the second end relative to the first end,
      the active position at least one of:
         preventing posterior displacement of the second end relative to the first end, and
         positioning the second end of the implant anteriorly relative to the first end, wherein the implant comprises a first rigidity or a first stiffness when in the active position and a second rigidity or a second stiffness when in the inactive position, where the first rigidity or first stiffness is greater than the second rigidity or second stiffness; and
   an activation mechanism comprising any of a magnetic device, a electromagnetic device, a spring, a piston, a pump, and a reservoir, the activation mechanism enabling transition between the inactive position and the active position based on a force of the implant coupled to the first pivot device and the second pivot device.

2. The apparatus of claim 1 wherein,
   the implant comprises a longitudinal axis extending from the first end to the second end; and
   the activation mechanism comprises at least one of:
      a change in a position of the longitudinal axis between a generally horizontal position and a generally vertical position;
      compression of air, fluid, or foam:
      moving at least a portion of one or more of the implant, the first pivot device, and the second pivot device; and
      one of a magnetic and an electromagnetic device.

3. The apparatus of claim 2, wherein the implant comprises the active position when at least one of:
   the longitudinal axis is in a generally vertical position; and
   the patient is in a horizontal or substantially horizontal position.

4. The apparatus of claim 2, wherein changing a position of the longitudinal axis between a generally horizontal position and a generally vertical position comprises changing a position of a skull of the patient.

5. The apparatus of claim 1, wherein, when the implant is in the active position, one or more of a patient's tongue, soft tissues of mouth, and soft tissues of throat are maintained in a neutral position or an anterior position; and
   obstruction of the upper airway of the patient is prevented.

6. The apparatus of claim 1, wherein
the implant comprises the chain;
the chain comprises a slack orientation in the inactive position and a taut orientation in the active position:
the taut orientation applies a biasing force that displaces the lower jaw anteriorly relative
to the mastoid bone or the temporal bone, wherein the biasing force is applied on the second pivot device:
the activation mechanism mechanically or magnetically activates the implant,
the mechanical activation comprises:
an automatic activation when an angle between the implant and a patient longitudinal axis exceeds a threshold angle,
a manual activation by action of the user, or
manually triggered via the spring or the piston coupled to the implant; and
magnetic activation comprises a magnetic field strength at or near a first magnetic device coupled to the implant exceeding a threshold magnetic field strength, wherein the magnetic field strength is generated by a second magnetic device.

7. The apparatus of claim 1, wherein
the implant comprises the spring:
the spring comprises a non-linear load or a non-linear k-value:
in the inactive position the spring applies one of a first biasing force and a zero biasing force on the lower jaw; and
in the active position, the spring applies a second biasing force on the lower jaw the second biasing force comprising a force that is at least one of, greater than the first biasing force, and
along a different direction than a direction associated with the first biasing force.

8. The apparatus of claim 1, wherein
the implant comprises an inflatable member:
the inflatable member inflates in the active position and at least partially deflates in the inactive position:
in the inactive position, the inflatable member applies one of a first biasing force and a zero biasing force on a lower jaw;
in the active position, the inflatable member applies a second biasing force on the lower jaw, the second biasing force comprising a force that is at least one of, greater than the first biasing force, and
along a different direction than a direction associated with the first biasing force:
and
the activation mechanism activates the implant by inflating the inflatable member with air or a fluid.

9. The apparatus of claim 1, wherein
the implant comprises the spacer, the spacer configured to couple to a distal portion of the mastoid or the temporal bone and a proximal portion of the mandible bone; and
the spacer comprises a shape and a size to extend between a gap between the distal portion of the mastoid or the temporal bone and the proximal portion of the mandible bone.

10. The apparatus of claim 9, wherein
the spacer comprises an inflatable material;
the inflatable material inflates when in the active position; and
the spacer displaces the mandible bone anteriorly relative to the mastoid bone or the temporal bone when in the active position.

11. The apparatus of claim 1, wherein the activation mechanism transitions the implant to the active position based on one or more of:
a mechanical activation, the mechanical activation at least one of:
manually triggered by an action, or
automatically triggered when an angle between the implant and a patient longitudinal axis exceeds a threshold angle;
a magnetic activation, the magnetic activation triggered by a magnetic field strength at or near a first magnetic device coupled to the implant exceeding a threshold magnetic field strength,
wherein the magnetic field strength is generated by a second magnetic device;
a spring activation, the spring activation triggered by the spring coupled to the implant; and
a piston activation, the piston activation triggered by the piston coupled to the implant.

12. The apparatus of claim 1, wherein the first pivot device is coupled to, or proximal to, a lower jaw of the patient and posterior to the second pivot device.

13. The apparatus of claim 1, wherein the second pivot device is configured to anchor at or near an angle of the mandible bone or a lower portion of the mandible bone.

14. An apparatus comprising:
a first pivot device configured to anchor to at least one of a mastoid bone and a temporal bone;
a second pivot device configured to anchor to a mandible bone;
an implant positioned between the first pivot device and the second pivot device; and wherein the implant comprises,
a first end of the implant configured to be coupled to the first pivot device,
a second end of the implant configured to be coupled to the second pivot device,
the implant comprising a post, the post comprises a non-linear load or a non-linear k-value:
the post displaces the mandible bone or a lower jaw forward relative to the mastoid bone or the temporal bone when the implant is in an active position;
the implant configured to be disposed in an inactive position or the active position, the inactive position enabling a posterior displacement of the second end relative to the first end,
the active position at least one of preventing posterior displacement of the second end relative to the first end and positioning the second end of the implant anteriorly relative to the first end; and
an activation mechanism comprising any of a magnetic device, an electromagnetic device, a spring, a piston, a pump, and a reservoir, the activation mechanism enabling transition between the inactive position and the active position based on a force of the implant coupled to the first pivot device and the second pivot device, the activation mechanism mechanically or magnetically activates the implant:
mechanical activation comprises:
an automatic activation when an angle between the implant and a patient longitudinal axis exceeds a threshold angle, or
a manual activation by an action; and
magnetic activation comprises a magnetic field strength at or near a first magnetic device coupled to the implant exceeding a threshold magnetic field strength, wherein the magnetic field strength is generated by a second magnetic device.

15. The apparatus of claim 14, wherein the implant comprises a longitudinal axis extending from the first end to the second end; and
the activation mechanism comprises at least one of:
a change in a position of the longitudinal axis between a generally horizontal position and a generally vertical position:
compression of air, fluid, or foam:
moving at least a portion of one or more of the implant, the first pivot device, and the second pivot device; and
one of a magnetic and an electromagnetic device.

16. The apparatus of claim 15, wherein the implant comprises the active position when at least one of:
the longitudinal axis is in a generally vertical position; and
a patient is in a horizontal or substantially horizontal position.

17. The apparatus of claim 15, wherein changing a position of the longitudinal axis between a generally horizontal position and a generally vertical position comprises changing a position of a skull of a patient.

18. The apparatus of claim 14, wherein, when the implant is in the active position, one or more of a tongue, soft tissues of mouth, and soft tissues of throat of a patient are configured to be maintained in a neutral position or an anterior position; and
obstruction of the upper airway of the patient is prevented.

19. The apparatus of claim 14, wherein the activation mechanism transitions the implant to the active position based on one or more of:
a mechanical activation, the mechanical activation at least one of:
manually triggered by an action, or
automatically triggered when an angle between the implant and a patient longitudinal axis exceeds a threshold angle;
a magnetic activation, the magnetic activation triggered by a magnetic field strength at or near a first magnetic device coupled to the implant exceeding a threshold magnetic field strength,
wherein the magnetic field strength is generated by a second magnetic device;
a spring activation, the spring activation triggered by the spring coupled to the implant; and
a piston activation, the piston activation triggered by the piston coupled to the implant.

20. The apparatus of claim 14, wherein the second pivot device is configured to anchor at or near an angle of a mandible bone or a lower portion of the mandible bone.

21. The apparatus of claim 14, wherein the implant comprises an inflatable member;
the inflatable member inflates in the active position and at least partially deflates in the inactive position;
in the inactive position, the inflatable member applies one of a first biasing force and a zero biasing force on the lower jaw;
in the active position, the inflatable member applies a second biasing force on the lower jaw, the second biasing force comprising a force that is at least one of, greater than the first biasing force, and
along a different direction than a direction associated with the first biasing force; and the activation mechanism activates the implant by inflating the inflatable member with air or a fluid.

22. A system for relieving upper airway obstructive breathing in a patient, the system comprising:
a first pivot device configured to be anchored to at least one of a mastoid bone and a temporal bone of the patient:
a second pivot device configured to be anchored to a mandible bone of the patient:
an implant positioned between the first pivot device and the second pivot device, the implant comprising any of a spring, a cylindrical post, a chain, and a spacer; and
wherein the implant comprises,
a first end of the implant configured to be coupled to the first pivot device,
a second end of the implant configured to be coupled to the second pivot device,
an inactive position, the inactive position enabling a posterior displacement of the second end relative to the first end, and
an active position, the active position at least one of:
preventing posterior displacement of the second end relative to the first end, and
positioning the second end of the implant anteriorly relative to the first end, wherein the implant comprises a first rigidity or a first stiffness when in the active position and a second rigidity or a second stiffness when in the inactive position, wherein the first rigidity or first stiffness is greater than the second rigidity or second stiffness:
an activation mechanism enabling transition between the inactive position and the active position based on a force of the implant coupled to the first pivot device and the second pivot device; and wherein:
the activation mechanism is coupled to or in communication with the implant,
the activation mechanism comprises at least one of:
a magnetic or an electromagnetic device,
a spring,
a piston assembly,
a pump, and
a reservoir, and
at least a portion of the activation mechanism is positioned in an interior of the patient.

23. The system of claim 22 wherein,
the implant comprises a longitudinal axis extending from the first end to the second end; and
the activation mechanism comprises at least one of:
a change in a position of the longitudinal axis between a generally horizontal position and a generally vertical position;
compression of air, fluid, or foam;
moving at least a portion of one or more of the implant, the first pivot device, and the second pivot device; and
one of a magnetic and an electromagnetic device.

24. The system of claim 22, wherein the first pivot device is configured to be coupled to, or proximal to, a lower jaw of the patient and posterior to the second pivot device.

25. A method for relieving upper airway obstructive breathing in a patient, the method comprising:
anchoring a first pivot device to at least one of a mastoid bone or a temporal bone of the patient;
anchoring a second pivot device to a mandible bone of the patient; and positioning an implant between the first pivot device and the second pivot device, wherein the implant comprises,
  a first end coupled to the first pivot device,
  a second end coupled to the second pivot device,
  a longitudinal axis extending from the first end to the second end,
  a first rigidity or a first stiffness when in an active position and a second rigidity or a second stiffness when in an inactive position, wherein the first rigidity or first stiffness is greater than the second rigidity or second stiffness the inactive position comprising the longitudinal axis in a generally horizontal position, the inactive position enabling a posterior displacement of the second end relative to the first end, and
  the active position comprising the longitudinal axis in a generally vertical position,
the active position at least one of:
  preventing posterior displacement of the second end relative to the first end, and
  positioning the second end of the implant anteriorly relative to the first end; and
  transitioning the implant between the inactive position and the active position, and vice-versa.

26. The method of claim 25, further comprising an activation mechanism wherein the activation mechanism enables the transitioning between the inactive position and the active position, and vice versa, and wherein, when the implant is in the active position, one or more of a patient's tongue, soft tissues of mouth, and soft tissues of throat are maintained in a neutral position or an anterior position thereby preventing obstruction of the upper airway of the patient.

27. The method of claim 25, wherein the first pivot device, the second pivot device, and the implant are surgically implanted in a patient's skull, mandible or lower jaw, or a combination thereof.

28. The method of claim 25,
  wherein the implant comprises any of a post, a chain link, and a spring:
  an inflatable member; or
  a spacer.

* * * * *